US012544511B2

(12) United States Patent
Koska et al.

(10) Patent No.: US 12,544,511 B2
(45) Date of Patent: Feb. 10, 2026

(54) SYSTEMS AND METHODS FOR PRE-FILLED DUAL-CHAMBER MEDICAL AGENT DELIVERY

(71) Applicant: Koska Family Limited, East Sussex (GB)

(72) Inventors: Marc Andrew Koska, East Sussex (GB); Jeff Price, Windermere, FL (US); Hanjin In, Toronto (CA); Jae-Hyok Cha, Gongju-si (KR)

(73) Assignee: Koska Family Limited, East (GB)

( * ) Notice: Subject to any disclaimer, the term of this patent is extended or adjusted under 35 U.S.C. 154(b) by 1122 days.

(21) Appl. No.: 17/129,593

(22) Filed: Dec. 21, 2020

(65) Prior Publication Data

US 2021/0128835 A1 May 6, 2021

Related U.S. Application Data

(63) Continuation-in-part of application No. PCT/US2019/038302, filed on Jun. 20, 2019.

(Continued)

(51) Int. Cl.

*A61M 5/19* (2006.01)
*A61J 1/06* (2006.01)
*A61M 5/32* (2006.01)

(52) U.S. Cl.

CPC ................ *A61M 5/19* (2013.01); *A61J 1/067* (2013.01); *A61M 5/3202* (2013.01); *A61M 5/3293* (2013.01)

(58) Field of Classification Search

CPC ........ A61J 1/067; A61J 1/2096; A61J 1/2089; A61J 1/2093; A61M 2005/3128;

(Continued)

(56) References Cited

U.S. PATENT DOCUMENTS 2,667,165 A 1/1954 Smith
2,717,598 A 9/1955 Krasno (Continued)

FOREIGN PATENT DOCUMENTS

AU 2337470 6/1972
AU 2019203408 B2 9/2020

(Continued)

OTHER PUBLICATIONS

Communication prusuant to Article 94(3) EPC for EP 17730256.9 dated Aug. 31, 2022; 5 pps.

(Continued)

*Primary Examiner* — Michael J Tsai
*Assistant Examiner* — Kathleen Paige Farrell
(74) *Attorney, Agent, or Firm* — Rowan Tree Law Group, PLLC; Carson C.K. Fincham

(57) ABSTRACT

A pre-filled dual-chamber medical agent delivery system assembled and configured to allow delivery of a single dose of a combined therapeutic agent (e.g., vaccine, drug, medicament, etc.) from a Blow-Fill-Seal (BFS) vial to a patient. The delivery assembly generally includes a modular design consisting of separately constructed components cooperatively arranged and coupled to one another, such as to facilitate delivery of a reconstituted lyophilized agent to a patient.

20 Claims, 20 Drawing Sheets

Related U.S. Application Data

(60) Provisional application No. 63/076,968, filed on Sep. 11, 2020, provisional application No. 62/687,340, filed on Jun. 20, 2018.

(58) Field of Classification Search
CPC .... A61M 5/3293; A61M 5/19; A61M 5/3202; A61M 5/282; A61M 5/284; A61M 5/288; A61M 5/3129; A61M 5/3294; A61M 5/345; A61M 5/30; A61M 5/2425; B29C 49/04; B29L 2031/7158; B65B 7/161
See application file for complete search history.

(56) References Cited

U.S. PATENT DOCUMENTS

| | | | |
|---|---|---|---|
| 2,737,948 A | | 3/1956 | Brown |
| 2,828,743 A | | 4/1958 | Ashkenaz |
| 3,073,307 A | | 1/1963 | Stevens |
| 3,192,925 A | | 7/1965 | Cunningham |
| 3,251,915 A | | 5/1966 | Pechthold |
| 3,406,686 A | | 10/1968 | Keller |
| 3,491,757 A | | 1/1970 | Arce |
| 3,640,388 A | | 2/1972 | Ferrari |
| 3,917,120 A | | 11/1975 | Larenz |
| 3,989,045 A | | 11/1976 | Van Eck |
| 4,018,222 A | | 4/1977 | Mcaleer |
| 4,022,206 A | | 5/1977 | Hilleman |
| 4,130,117 A | | 12/1978 | Van Eck |
| 4,502,616 A | | 3/1985 | Meierhoefer |
| 4,539,172 A | | 9/1985 | Winchell |
| 4,643,309 A | | 2/1987 | Evers |
| 4,671,763 A | | 6/1987 | Weiler |
| 4,883,473 A | | 11/1989 | Thomas |
| 4,955,871 A | | 9/1990 | Thomas |
| 4,966,581 A | | 10/1990 | Landau |
| 4,979,630 A | | 12/1990 | Rose |
| 4,995,519 A | | 2/1991 | Rose |
| 5,112,311 A | | 5/1992 | Utterberg |
| 5,135,514 A | | 8/1992 | Kimber |
| 5,139,489 A | | 8/1992 | Hollister |
| 5,217,480 A | | 6/1993 | Haber |
| 5,222,948 A | | 6/1993 | Glenn et al. |
| 5,242,422 A | | 9/1993 | Schneberger |
| 5,261,881 A | | 11/1993 | Riner |
| 5,356,052 A | | 10/1994 | Poynter |
| 5,370,626 A | | 12/1994 | Farris |
| 5,374,263 A | | 12/1994 | Weiler |
| 5,395,365 A | | 3/1995 | Weiler |
| 5,409,125 A | | 4/1995 | Kimber |
| 5,427,275 A | | 6/1995 | Hansen |
| 5,503,885 A | | 4/1996 | Anderson |
| 5,509,906 A | | 4/1996 | Poynter |
| 5,533,505 A | | 7/1996 | Kallstrand |
| 5,624,407 A | | 4/1997 | Claro |
| 5,636,640 A | | 6/1997 | Staehlin |
| 5,761,885 A | | 6/1998 | Hansen |
| 5,944,699 A | * | 8/1999 | Barrelle .................. A61M 5/34 604/263 |
| 6,050,400 A | | 4/2000 | Taskis |
| D425,617 S | | 5/2000 | Snedden |
| 6,065,270 A | | 5/2000 | Reinhard |
| 6,068,148 A | | 5/2000 | Weiler |
| 6,120,478 A | | 9/2000 | Moore |
| 6,134,866 A | | 10/2000 | Schoenewolff |
| 6,173,852 B1 | | 1/2001 | Browne |
| 6,200,296 B1 | | 3/2001 | Dibiasi |
| 6,231,559 B1 | | 5/2001 | Loretti |
| 6,241,124 B1 | | 6/2001 | Hoyt |
| 6,258,063 B1 | | 7/2001 | Haar |
| D447,560 S | | 9/2001 | Hellberg |
| 6,332,876 B1 | | 12/2001 | Poynter |
| 6,357,626 B1 | | 3/2002 | Zhang |
| 6,379,342 B1 | | 4/2002 | Levinson |
| 6,383,166 B1 | | 5/2002 | Farris |
| D458,366 S | | 6/2002 | Hellberg |
| D462,760 S | | 9/2002 | Ahlgrim |
| D467,336 S | | 12/2002 | Gilbard |
| 6,517,768 B1 | | 2/2003 | Weiler |
| D471,628 S | | 3/2003 | Louviere |
| 6,585,134 B2 | | 7/2003 | Farris |
| 6,626,308 B2 | | 9/2003 | Weiler |
| D492,407 S | | 6/2004 | Masuda |
| 6,764,463 B1 | | 7/2004 | Farris |
| 6,777,052 B2 | | 8/2004 | Kai |
| 6,860,405 B1 | | 3/2005 | Poynter |
| 6,918,418 B1 | | 7/2005 | Farris |
| D517,207 S | | 3/2006 | Poynter |
| 7,028,862 B2 | | 4/2006 | Poynter |
| 7,029,465 B2 | | 4/2006 | Heyes |
| 7,100,600 B2 | | 9/2006 | Loeffler |
| 7,188,750 B2 | | 3/2007 | Vogel |
| 7,308,782 B2 | | 12/2007 | Hansen |
| 7,357,893 B2 | | 4/2008 | Hansen |
| D573,710 S | | 7/2008 | Goodman |
| 7,425,207 B2 | | 9/2008 | Miller |
| 7,438,704 B1 | | 10/2008 | Kawashima |
| 7,487,894 B2 | | 2/2009 | Zahn |
| 7,513,397 B2 | | 4/2009 | Zahn |
| 7,562,796 B2 | | 7/2009 | Zahn |
| 7,632,253 B2 | | 12/2009 | Ooyauchi |
| D618,339 S | | 6/2010 | Hansen |
| 7,832,594 B2 | | 11/2010 | Yamada |
| 7,832,601 B2 | | 11/2010 | Zahn |
| 7,866,514 B1 | | 1/2011 | Hansen |
| 7,883,660 B2 | | 2/2011 | Matsuda et al. |
| 7,892,211 B2 | | 2/2011 | McCulloch |
| 7,892,614 B2 | | 2/2011 | Radermacher |
| 7,993,304 B2 | | 8/2011 | Kriesel |
| 8,087,524 B2 | | 1/2012 | Hansen |
| 8,133,202 B2 | | 3/2012 | Marsh |
| D674,481 S | | 1/2013 | Decoste |
| 8,377,029 B2 | | 2/2013 | Nagao |
| D681,196 S | | 4/2013 | Henrikson |
| 8,431,068 B2 | | 4/2013 | Hansen |
| 8,434,643 B2 | | 5/2013 | Harris |
| 8,464,918 B1 | | 6/2013 | Harris |
| 8,486,043 B2 | | 7/2013 | Iyer |
| 8,486,501 B2 | | 7/2013 | Manabe |
| 8,551,053 B2 | | 10/2013 | Hansen |
| 8,640,873 B2 | | 2/2014 | Nakano |
| 8,652,096 B2 | | 2/2014 | Alvey |
| 8,663,188 B2 | | 3/2014 | Genosar |
| 8,672,885 B2 | | 3/2014 | Kriesel |
| D710,993 S | | 8/2014 | Decoste |
| 8,795,226 B2 | | 8/2014 | Kuhn et al. |
| 8,857,470 B2 | | 10/2014 | Rahimy |
| D721,434 S | | 1/2015 | Mulvey |
| 8,967,140 B2 | | 3/2015 | Denyer |
| 8,986,236 B2 | | 3/2015 | Slokovic |
| D731,642 S | | 6/2015 | Cehajic |
| 9,079,686 B2 | | 7/2015 | Domkowski |
| 9,095,500 B2 | | 8/2015 | Brandenburger |
| 9,108,777 B1 | | 8/2015 | Santamarta |
| 9,132,238 B2 | | 9/2015 | Ferreri |
| 9,150,317 B2 | | 10/2015 | Hansen |
| 9,168,201 B2 | | 10/2015 | Mcaffer |
| 9,216,477 B2 | | 12/2015 | Gibson |
| 9,242,051 B2 | | 1/2016 | Jugl et al. |
| 9,248,076 B2 | | 2/2016 | Sullivan |
| 9,265,889 B2 | | 2/2016 | Thornton |
| D753,292 S | | 4/2016 | Oathes, II |
| 9,314,403 B2 | | 4/2016 | Smith |
| 9,358,738 B2 | | 6/2016 | Wolters |
| 9,364,393 B1 | | 6/2016 | Grabowski |
| 9,399,102 B2 | | 7/2016 | Dewoolfson |
| 9,526,839 B2 | | 12/2016 | Chia |
| D776,266 S | | 1/2017 | Dombrowski |
| 9,533,065 B2 | | 1/2017 | Foreman |
| D779,653 S | | 2/2017 | Habig |
| 9,592,354 B2 | | 3/2017 | Sullivan |
| 9,597,259 B2 | | 3/2017 | Becker |
| 9,737,664 B2 | | 8/2017 | Gardner |
| 9,808,608 B2 | | 11/2017 | Webb |
| 9,820,913 B2 | | 11/2017 | Genosar |

(56) References Cited

U.S. PATENT DOCUMENTS 9,828,148 B2 11/2017 Schreckenhoefer
9,908,682 B2 3/2018 Mcaffer
9,918,900 B2 3/2018 Hansen
9,987,790 B2 6/2018 Suyama
10,018,536 B2 7/2018 Huschke
10,039,884 B2 8/2018 Ferreri
10,064,785 B2 9/2018 Spallek
10,086,984 B2 10/2018 Colangelo
10,098,814 B2 10/2018 Spallek
10,105,491 B2 10/2018 Gelblum
10,117,994 B2 11/2018 Holtwick
10,118,000 B2 11/2018 Schraga
10,147,268 B2 12/2018 Walker
10,149,939 B2 12/2018 Giambattista et al.
10,155,088 B2 12/2018 Basile
10,155,829 B2 12/2018 Destro
10,207,053 B2 2/2019 Groskoff et al.
10,278,896 B2 5/2019 Brandenburger
10,315,788 B2 6/2019 Consolaro
10,335,507 B2 7/2019 Reed
10,342,735 B2 7/2019 Chou
10,351,272 B2 7/2019 Colangelo
10,363,369 B2 7/2019 Cosman
D859,647 S 9/2019 Chang
10,456,328 B2 10/2019 Brandenburger
10,464,708 B2 11/2019 Geser
10,471,244 B2 11/2019 Dombrowski
10,500,338 B2 12/2019 Berenshteyn
10,512,591 B2 12/2019 Oshgan et al.
10,525,212 B2 1/2020 Thornton
10,543,317 B2 1/2020 Basile
10,543,944 B2 1/2020 Batema
10,583,256 B2 3/2020 Berry
10,589,075 B2 3/2020 Wills
10,639,839 B2 5/2020 Consolaro
10,716,901 B2 7/2020 Genosar
10,737,840 B2 8/2020 Oates, II
10,765,849 B2 9/2020 Chiang
D898,901 S 10/2020 De Malibran-Santibanez
10,793,323 B2 10/2020 Cosman
10,821,053 B2 11/2020 Rajagopal et al.
10,828,860 B2 11/2020 Vaes
10,874,588 B2 12/2020 Schabbach
10,888,454 B2 1/2021 Ivri
10,918,809 B2 2/2021 Ferreri
10,928,236 B2 2/2021 Adler
10,933,190 B2 3/2021 Berry
10,940,633 B2 3/2021 Schubert
10,961,003 B2 3/2021 Banuelos
10,967,126 B2 4/2021 Holtwick
10,981,713 B2 4/2021 Genosar
11,027,862 B2 6/2021 Wong
11,059,638 B2 7/2021 Spallek
11,077,263 B2 8/2021 Loenner
11,123,499 B2 9/2021 Basile
11,136,148 B2 10/2021 Rehbein
11,167,889 B2 11/2021 Ikeda
11,173,022 B2 11/2021 De Malibran-Santibanez
11,185,634 B2 * 11/2021 Genosar .............. A61M 5/2425
11,191,910 B2 12/2021 Hoekman
11,198,243 B2 12/2021 Beck
D943,092 S 2/2022 Buehrle
11,279,098 B2 3/2022 Groh
11,285,504 B2 3/2022 Wilkerson
D952,137 S 5/2022 Chandrapati
11,324,660 B2 5/2022 Geser
D954,943 S 6/2022 Byron
11,351,090 B2 6/2022 Brandenburger
11,351,715 B2 6/2022 Sauter
11,353,406 B2 6/2022 Prinz
11,377,263 B2 7/2022 Gydesen
11,382,833 B2 7/2022 Koska
11,396,123 B2 7/2022 Hoshino
11,400,241 B2 8/2022 Patton
11,400,637 B2 8/2022 Shiokawa
11,400,638 B2 8/2022 Hoshino
11,419,984 B2 8/2022 Schabbach
11,446,209 B2 9/2022 Barkman
11,446,856 B2 9/2022 Furlotti
11,534,551 B2 12/2022 Ferreri
11,565,838 B2 1/2023 Meier
11,591,126 B2 2/2023 Köppel
11,607,369 B2 3/2023 Koska
11,638,783 B2 5/2023 Consolaro
11,648,180 B2 5/2023 Genosar
D992,110 S 7/2023 Price
2002/0104856 A1 8/2002 Clark
2003/0050602 A1 3/2003 Pettis et al.
2003/0186456 A1 10/2003 Stroup
2004/0015131 A1 1/2004 Flaherty
2004/0118477 A1 6/2004 Desmond
2005/0049560 A1 3/2005 Hauri
2006/0032189 A1 2/2006 Giacobbe
2006/0073173 A1 4/2006 Banach
2006/0108385 A1 * 5/2006 Zahn ....................... A61J 1/067
222/541.9
2007/0167904 A1 7/2007 Zinger
2007/0191780 A1 8/2007 Modi
2007/0260188 A1 11/2007 Kelly et al.
2008/0000798 A1 1/2008 Gutmann
2008/0083691 A1 4/2008 Poynter
2008/0228162 A1 * 9/2008 Trager .................... A61J 1/067
604/407
2008/0243077 A1 10/2008 Bivin
2008/0258334 A1 10/2008 Hansen
2008/0262466 A1 10/2008 Smith
2009/0025823 A1 1/2009 Hansen
2009/0171311 A1 7/2009 Genosar
2009/0216212 A1 8/2009 Fangrow, Jr.
2009/0230077 A1 9/2009 Poynter
2009/0230080 A1 9/2009 Hansen
2010/0163577 A1 7/2010 Hansen
2010/0249716 A1 9/2010 Wong
2011/0031157 A1 2/2011 Nakano
2011/0131929 A1 6/2011 Mcaffer
2011/0135720 A1 6/2011 Seabrook, Jr. et al.
2011/0160677 A1 6/2011 March
2011/0186451 A1 8/2011 Dersjoe
2011/0224640 A1 9/2011 Kuhn et al.
2012/0027818 A1 2/2012 Glausch
2012/0074001 A1 3/2012 Amir
2012/0078215 A1 * 3/2012 Finke .................... A61J 1/2096
264/255
2012/0083744 A1 4/2012 Finke et al.
2012/0179109 A1 7/2012 Takemoto et al.
2012/0238962 A1 9/2012 Chin
2013/0015204 A1 1/2013 Gol
2013/0098864 A1 * 4/2013 Fontana ................. B65D 1/095
215/250
2013/0104324 A1 5/2013 Greer, Jr.
2013/0110053 A1 5/2013 Yoshino et al.
2013/0345672 A1 12/2013 Ferreri
2013/0345673 A1 12/2013 Ferreri
2014/0008366 A1 1/2014 Genosar
2014/0039444 A1 2/2014 Togawa
2014/0046270 A1 2/2014 Thornton
2014/0054295 A1 2/2014 Holtwick
2014/0069839 A1 3/2014 Colin
2014/0188502 A1 7/2014 Defrank
2014/0224815 A1 8/2014 Gallem
2014/0231456 A1 8/2014 Marshall
2014/0291278 A1 10/2014 Colin
2014/0323975 A1 10/2014 Thornton et al.
2015/0136622 A1 5/2015 Genosar
2015/0165123 A1 6/2015 Thornton
2015/0202372 A1 7/2015 Ali
2015/0283332 A1 10/2015 Woehr
2015/0297837 A1 10/2015 Schraga
2015/0359708 A1 12/2015 Boomgard
2016/0022541 A1 1/2016 Dalal
2016/0063215 A1 3/2016 Zamer
2016/0074586 A1 3/2016 Mernoe et al.
2016/0120749 A1 5/2016 Hansen
2016/0144130 A1 5/2016 Thornton

(56) References Cited

U.S. PATENT DOCUMENTS

| | | | |
|---|---|---|---|
| 2016/0151240 | A1 | 6/2016 | Brandenburger |
| 2016/0175544 | A1 | 6/2016 | Koska |
| 2016/0206417 | A1 | 7/2016 | Levine |
| 2016/0246943 | A1 | 8/2016 | Lake |
| 2016/0354537 | A1 | 12/2016 | Jozwik |
| 2017/0007767 | A1 | 1/2017 | Schabbach |
| 2017/0128676 | A1 | 5/2017 | Spallek |
| 2018/0072480 | A1 | 3/2018 | Genosar |
| 2018/0153772 | A1 | 6/2018 | Spallek |
| 2018/0193565 | A1 | 7/2018 | Koska |
| 2018/0193571 | A1 | 7/2018 | Koska |
| 2018/0193572 | A1 | 7/2018 | Koska |
| 2018/0197143 | A1 | 7/2018 | Daub |
| 2018/0235839 | A1 | 8/2018 | Johnson |
| 2018/0235840 | A1 | 8/2018 | Genosar |
| 2018/0280234 | A1 | 10/2018 | Brevik-Andersen |
| 2019/0009068 | A1 | 1/2019 | Margoosian |
| 2019/0046402 | A1 | 2/2019 | Besbrosses et al. |
| 2019/0060168 | A1 | 2/2019 | Koska |
| 2019/0060573 | A1 | 2/2019 | Consolaro et al. |
| 2019/0156931 | A1 | 5/2019 | Skoda |
| 2019/0214116 | A1 | 7/2019 | Eberting |
| 2019/0224424 | A1 | 7/2019 | Helmer et al. |
| 2020/0100985 | A1 | 4/2020 | Auerbach |
| 2020/0118164 | A1 | 4/2020 | Defrank |
| 2020/0129698 | A1 | 4/2020 | Chowdhury |
| 2020/0164563 | A1 | 5/2020 | Spallek |
| 2020/0172271 | A1 | 6/2020 | Colangelo |
| 2020/0246547 | A1 * | 8/2020 | Glenting ............... A61M 5/345 |
| 2020/0276082 | A1 | 9/2020 | Koska |
| 2020/0384186 | A1 | 12/2020 | Consolaro |
| 2021/0030965 | A1 | 2/2021 | Koska |
| 2021/0128835 | A1 | 5/2021 | Koska |
| 2021/0244888 | A1 | 8/2021 | Ryan |
| 2021/0353538 | A1 | 11/2021 | Humeniuk |
| 2022/0024616 | A1 | 1/2022 | Lema Martinez |
| 2022/0041317 | A1 | 2/2022 | Hammer |
| 2022/0133695 | A1 | 5/2022 | Terraz Mendoza |
| 2022/0203596 | A1 | 6/2022 | Yoshino |
| 2022/0273923 | A1 | 9/2022 | Zeira |
| 2022/0273924 | A1 | 9/2022 | Kamen |
| 2022/0315296 | A1 | 10/2022 | Gamboa Burgos |
| 2022/0323301 | A1 | 10/2022 | Koska |
| 2022/0336074 | A1 | 10/2022 | Bakos |
| 2022/0336076 | A1 | 10/2022 | Albertini |
| 2022/0371873 | A1 | 11/2022 | Hayakawa |
| 2022/0401300 | A1 | 12/2022 | Ikeda |
| 2022/0409830 | A1 | 12/2022 | Shahaf |
| 2023/0045719 | A1 | 2/2023 | Koska |
| 2023/0064428 | A1 | 3/2023 | Price |
| 2023/0081577 | A1 | 3/2023 | Walker et al. |
| 2023/0087192 | A1 | 3/2023 | Ferreri |
| 2023/0099753 | A1 | 3/2023 | Genosar |
| 2023/0141404 | A1 | 5/2023 | Price |
| 2023/0158255 | A1 | 5/2023 | Consolaro |
| 2023/0173178 | A1 | 6/2023 | Clapham |
| 2023/0190581 | A1 | 6/2023 | Hover |
| 2023/0192346 | A1 | 6/2023 | Bouteloup |
| 2023/0192367 | A1 | 6/2023 | Bisio |
| 2023/0201387 | A1 | 6/2023 | Shieu |
| 2023/0226276 | A1 | 7/2023 | Amiri |
| 2023/0226743 | A1 | 7/2023 | Schnell |
| 2023/0248897 | A1 | 8/2023 | Murray |
| 2023/0248957 | A1 | 8/2023 | Fuchs |
| 2024/0009397 | A1 | 1/2024 | In |
| 2024/0009398 | A1 | 1/2024 | Koska |
| 2024/0058217 | A1 | 2/2024 | Price |

FOREIGN PATENT DOCUMENTS

| | | | |
|---|---|---|---|
| CA | 2105031 | | 3/1994 |
| CN | 1196023 | A | 10/1998 |
| CN | 104640594 | | 5/2015 |
| CN | 112829265 | A | 5/2021 |
| CN | 115259051 | A | 11/2022 |
| CN | 217891819 | U | 11/2022 |
| CN | 217894251 | U | 11/2022 |
| CN | 218020077 | U | 12/2022 |
| EP | 0310227 | | 4/1989 |
| EP | 0388360 | | 9/1990 |
| EP | 0685400 | | 12/1995 |
| EP | 0849173 | A1 | 6/1998 |
| EP | 0903180 | | 3/1999 |
| EP | 0930238 | A1 | 7/1999 |
| EP | 1726285 | | 11/2006 |
| EP | 2665502 | | 7/2012 |
| EP | 2554201 | | 6/2013 |
| EP | 2554207 | | 6/2013 |
| EP | 2571553 | | 6/2014 |
| EP | 3173113 | | 5/2017 |
| EP | 3518860 | | 4/2018 |
| EP | 2919834 | | 5/2018 |
| FR | 2990687 | A1 | 11/2013 |
| GB | 2490111 | | 10/2012 |
| GB | 2495741 | | 4/2013 |
| GB | 2495741 | A | 4/2013 |
| IN | 201741030340 | | 1/2019 |
| JP | 2009183909 | A | 8/2009 |
| JP | 2015109883 | | 6/2015 |
| JP | 2019034072 | | 3/2019 |
| KR | 200345715 | | 3/2004 |
| KR | 100615527 | | 8/2006 |
| RU | 2643432 | | 2/2018 |
| WO | WO 1989/007462 | | 8/1989 |
| WO | WO 1993/017728 | | 9/1993 |
| WO | WO1997010156 | | 3/1997 |
| WO | WO1998025660 | | 6/1998 |
| WO | 1999043549 | | 9/1999 |
| WO | 0018648 | A1 | 4/2000 |
| WO | WO 2001/043799 | | 6/2001 |
| WO | 2004055143 | | 7/2004 |
| WO | 2007007178 | A1 | 1/2007 |
| WO | 2008086552 | | 7/2008 |
| WO | 2010081174 | | 7/2010 |
| WO | WO 2011/008190 | | 1/2011 |
| WO | 2011035503 | A1 | 3/2011 |
| WO | WO2011026050 | | 3/2011 |
| WO | WO 2011/075798 | | 6/2011 |
| WO | WO2012011115 | | 1/2012 |
| WO | 2012026551 | | 3/2012 |
| WO | WO2012064761 | | 5/2012 |
| WO | WO2012099898 | | 7/2012 |
| WO | 2012137945 | | 10/2012 |
| WO | 2012156822 | | 11/2012 |
| WO | WO2012148043 | | 11/2012 |
| WO | WO2013114357 | | 8/2013 |
| WO | 2013149042 | A1 | 10/2013 |
| WO | 2013162637 | A1 | 10/2013 |
| WO | WO20140035935 | | 3/2014 |
| WO | 2014135108 | | 9/2014 |
| WO | 2014135108 | A1 | 9/2014 |
| WO | 2014184121 | | 11/2014 |
| WO | 2014189761 | A1 | 11/2014 |
| WO | WO2015045740 | | 2/2015 |
| WO | WO2015036536 | | 3/2015 |
| WO | WO 2015/074087 | | 5/2015 |
| WO | 2015134307 | | 9/2015 |
| WO | 2015145902 | | 10/2015 |
| WO | 2015187518 | | 12/2015 |
| WO | 2015200261 | A1 | 12/2015 |
| WO | 2016032814 | | 3/2016 |
| WO | 2016097872 | | 6/2016 |
| WO | 2017001918 | | 1/2017 |
| WO | 2017001919 | | 1/2017 |
| WO | 2017001921 | | 1/2017 |
| WO | 2017001922 | | 1/2017 |
| WO | 2017001923 | | 1/2017 |
| WO | WO2017001925 | | 1/2017 |
| WO | 2017103954 | A1 | 6/2017 |
| WO | WO2017125859 | | 7/2017 |
| WO | 2017187262 | A1 | 11/2017 |
| WO | WO2017187262 | | 11/2017 |
| WO | 2018002113 | | 1/2018 |
| WO | 2018028820 | | 2/2018 |

(56) References Cited

FOREIGN PATENT DOCUMENTS

| | | |
|---|---|---|
| WO | 2019040575 A1 | 2/2019 |
| WO | 2019099954 | 5/2019 |
| WO | 2019108577 A1 | 6/2019 |
| WO | 2019154600 | 8/2019 |
| WO | 2019164478 | 8/2019 |
| WO | 2019246435 | 12/2019 |
| WO | 2020055960 A1 | 3/2020 |
| WO | 2021059213 | 4/2021 |
| WO | 2021079404 | 4/2021 |
| WO | 2021186485 | 9/2021 |
| WO | 2021186485 A1 | 9/2021 |
| WO | 2021207040 | 10/2021 |
| WO | 2021226564 | 11/2021 |
| WO | 2022002863 | 1/2022 |
| WO | 2022005310 | 1/2022 |
| WO | 2022026275 | 2/2022 |
| WO | 2022053948 | 3/2022 |
| WO | 2022091003 | 5/2022 |
| WO | 2022112543 | 6/2022 |
| WO | 2022117361 | 6/2022 |
| WO | 2022120269 | 6/2022 |
| WO | 2022133283 | 6/2022 |
| WO | 2022135945 | 6/2022 |
| WO | 2022115598 | 8/2022 |
| WO | 2022180376 | 9/2022 |
| WO | 2022180488 | 9/2022 |
| WO | 2022185350 | 9/2022 |
| WO | 2022186886 | 9/2022 |
| WO | 2022186888 | 9/2022 |
| WO | 2022204408 | 9/2022 |
| WO | 2022207136 | 10/2022 |
| WO | 2022208318 | 10/2022 |
| WO | 2022208488 | 10/2022 |
| WO | 2022256834 | 12/2022 |
| WO | 2022268253 | 12/2022 |
| WO | 2022269651 | 12/2022 |
| WO | 2023281194 | 1/2023 |
| WO | 2023018840 | 2/2023 |
| WO | 23045589 | 3/2023 |
| WO | 23045590 | 3/2023 |
| WO | 23049213 | 3/2023 |
| WO | 2023039126 | 3/2023 |
| WO | 2023045589 A1 | 3/2023 |
| WO | 2023045590 A1 | 3/2023 |
| WO | 2023049213 | 3/2023 |
| WO | 2023086515 A1 | 5/2023 |
| WO | 2023091358 | 5/2023 |
| WO | 2023102008 | 6/2023 |
| WO | 2023104995 | 6/2023 |
| WO | 2023122619 | 6/2023 |
| WO | 2023147491 | 8/2023 |
| WO | 2023244561 | 12/2023 |
| WO | 2024163988 | 8/2024 |

OTHER PUBLICATIONS

International Search Report for Application PCT/US22/40006 dated Nov. 7, 2022; 5 pps.
International Search Report for Application PCT/US22/44291 dated Dec. 22, 2022; 5 pps.
Office Action (Final Rejection) dated Dec. 28, 2022 for U.S. Appl. No. 16/876,417 (pp. 1-6).
Office Action (Notice of Allowance and Fees Due (PTOL-85)) dated May 17, 2022 for U.S. Appl. No. 16/169,983; 7 pps.
Office Action for U.S. Appl. No. 16/876,417 dated Jun. 8, 2022; 9 pps.
Written Opinion for Application PCT/US22/44291 dated Dec. 22, 2022; 5 pps.
Written Opinion for PCT/US22/40006 dated Nov. 7, 2022; 6 pps.
Allowance Notification for Chinese Application 201680050853.3 dated Jun. 8, 2021; 1 pp.
Allowance Notification for Chinese Application 201780025582.0 dated Jun. 21, 2021; 1 pp.
International Search Report for Application PCT/IB2016/001033 dated Dec. 9, 2016; 4 pps.
International Search Report for Application PCT/IB2016/001034 dated Dec. 13, 2016; 3 pps.
International Search Report for Application PCT/IB2016/001042 dated Dec. 22, 2016; 3 pps.
International Search Report for Application PCT/IB2021/058168 dated Nov. 11, 2021; 6 pps.
International Search Report for Application PCT/IB2021/058168 dated Nov. 22, 2021; 6 pps.
International Search Report for Application PCT/IB2021/059993 dated Nov. 22, 2021; 8 pps.
International Search Report for Application PCT/US2021/025683 dated Jul. 8, 2021; 2 pps.
International Search Report for Application PCT/US21/042671 dated Nov. 5, 2021; 2 pps.
International Search Report for Application PCT/US21/064155 dated Mar. 21, 2022; 2 pps.
International Search Report for Application PCT/US21/31452 dated Sep. 1, 2021; 2 pps.
International Search Report for Application PCT/US21/61991 dated Feb. 16, 2022; 2 pps.
Notice of Acceptance for Australian Application 2017256152 dated Apr. 11, 2022; 3 pps.
Office Action (Final) for U.S. Appl. No. 14/575,635 dated Dec. 14, 2017; 44 pps.
Office Action (Non-Final Rejection) dated Jan. 12, 2022 for U.S. Appl. No. 16/169,983 (pp. 1-12).
Office Action (Non-final) for U.S. Appl. No. 14/575,635 dated Mar. 23, 2017; 44 pps.
Office Action (Non-final) for U.S. Appl. No. 14/575,635 dated Oct. 9, 2018; 39 pps.
Office Action (Non-final) for U.S. Appl. No. 15/741,009 dated Oct. 2, 2019; 6 pps.
Office Action (Non-final) for U.S. Appl. No. 15/741,011 dated Oct. 2, 2019; 8 pps.
Office Action (Notice of Allowance and Fees Due (PTOL-85)) dated Feb. 23, 2022 for U.S. Appl. No. 16/169,983 (pp. 1-7).
Office Action (Notice of Allowance and Fees Due (PTOL-85)) dated Jul. 10, 2020 for U.S. Appl. No. 15/741,012 (pp. 1-6).
Office Action for Australian Application 2017256152 dated Jul. 29, 2021; 6 pps.
Office Action for Australian Application 2017256152 dated Nov. 12, 2021; 4 pps.
Office Action for Chinese Application 201680050853.3 dated Mar. 18, 2020; 3 pps.
Office Action for Chinese Application 201680050853.3 dated Nov. 27, 2020; 3 pps.
Office Action for Chinese Application 201780025582.0 dated Oct. 30, 2020; 2 pps.
Office Action for Chinese Application 201880087016.7 dated Feb. 24, 2022; 7 pps.
Office Action for Chinese Application 201880087016.7 dated Sep. 14, 2021; 3 pps.
Office Action for Indian Application 201827038286 dated Aug. 6, 2021; 6 pps.
Office Action for Indian Application 201827038286 dated Jul. 2, 2021; 8 pps.
Office Action for Korean Patent Application No. 10-2018-7030866 dated Mar. 30, 2022; 4 pps.
Office Action for Korean Patent Application No. 10-2018-7030866 dated Sep. 24, 2021; 17 pps.
Office Action for Mexican Application MX/a/2018/000257 dated Mar. 2, 2022; 5 pps.
Search Report for European Application 18877931.8 dated Jul. 7, 2021; 9 pps.
Search Report for European Application 18877931.8 dated Oct. 19, 2021; 10 pps.
Supplemental European Search Report for European Application No. 19823345.4 dated Feb. 7, 2022; 6 pps.
Written Opinion for Application PCT/IB2021/058168 dated Nov. 11, 2021; 9 pps.

(56) References Cited

OTHER PUBLICATIONS

Written Opinion for Application PCT/IB2021/059993 dated Nov. 22, 2021; 10 pps.
Written Opinion for Application PCT/US2021/025683 dated Jul. 8, 2021; 4 pps.
Written Opinion for Application PCT/US21/042671 dated Nov. 5, 2021; 9 pps.
Written Opinion for Application PCT/US21/31452 dated Sep. 1, 2021; 15 pps.
Written Opinion for Application PCT/US21/61991 dated Feb. 16, 2022; 9 pps.
Written Opinion for PCT/IB2021/058168 dated Nov. 22, 2021; 9 pps.
Written Opinion for PCT/US21/064155 dated Mar. 21, 2022; 3 pps.
Bufus Plastic Drop https://www.alamy.com/stock-photo-bufus-plastic-drop-ampoule-vial-spray-the-medicine-cast-resin-sealed 131358830.html Nov. 10, 2015 (Year: 2015).
International Search Report for Application PCT/US2022/49608 dated Feb. 21, 2023; 3 pps.
Notice of Allowance dated Mar. 21, 2023 for U.S. Appl. No. 29/803,121 (pp. 1-9).
Notice of Allowance dated May 5, 2023 for U.S. Appl. No. 29/803,121 (pp. 1-2).
Office Action (Notice of Allowance and Fees Due (PTOL-85)) dated Feb. 2, 2023 for U.S. Appl. No. 16/876,417 (pp. 1-5).
Woodstock Sterile Solutions https://woodstocksterilesolutions.com/manufacturing-capability/ Date Accessed Mar. 3, 2023 (Year: 2023).
Written Opinion for Application PCT/US2022/49608 dated Feb. 16, 2023; 6 pps.
Office Action (Non-Final Rejection) dated Jun. 8, 2022 for U.S. Appl. No. 16/876,417 (pp. 1-9).
Office Action (Notice of Allowance and Fees Due (PTOL-85)) dated May 17, 2022 for U.S. Appl. No. 16/169,983 (pp. 1-7).
Office Action (Notice of Allowance and Fees Due (PTOL-85)) dated Jun. 2, 2022 for U.S. Appl. No. 16/169,983 (pp. 1-3).
Office Action for Mexican Application MX/a/2018/000258 dated Jul. 6, 2022; 3 pps.
Office Action for Mexican Application MX/a/2018/000258 dated Jul. 18, 2022; 5 pps.
Australian Application 2022203652 dated Oct. 20, 2023; 7 pps.
Final Office Action dated Dec. 21, 2023 for U.S. Appl. No. 17/849,780; 13 pgs.
Final Office Action for U.S. Appl. No. 15/741,012 dated Oct. 2, 2019; 7 pps.
Final Office Action for U.S. Appl. No. 14/575,635 dated Dec. 14, 2017; 16 pps.
Final Office Action for U.S. Appl. No. 16/876,417 dated Dec. 28, 2022; 6 pps.
International Search Report for PCT Application No. PCT/US21/064155 dated Mar. 21, 2022; 2 pps.
International Search Report for PCT/IB2015/002531 dated Jan. 5, 2017; 3 pps.
International Search Report for PCT/IB2016/001026 dated Jan. 5, 2017; 4 pps.
International Search Report for PCT/IB2016/001027 dated Jan. 5, 2017; 3 pps.
International Search Report for PCT/US23/25123 dated Sep. 29, 2023; 2 pps.
International Written Opinion for PCT Application No. PCT/US21/064155 dated Mar. 21, 2022; 3 pps.
Notice of Allowance for U.S. Appl. No. 17/072,498 dated Jun. 30, 2023; 7 pgs.
Notice of Allowance dated Jun. 30, 2023 for U.S. Appl. No. 17/072,498 (pp. 1-7).
Notice of Allowance for U.S. Appl. No. 15/741,012 dated Jul. 10, 2020; 7 pps.
Notice of Allowance for U.S. Appl. No. 16/876,417 dated Feb. 2, 2023; 5 pps.
Notice of Hearing for Indian Application 201827038286 dated Jan. 17, 2024; 2 pps.
Office Action (Final Rejection) dated Dec. 21, 2023 for U.S. Appl. No. 17/849,780 (pp. 1-13).
Office Action (Non-Final Rejection) dated Feb. 7, 2023 for U.S. Appl. No. 17/072,498 (pp. 1-9).
Office Action (Non-Final Rejection) dated Aug. 8, 2023 for U.S. Appl. No. 17/849,780 (pp. 1-15).
Office Action (Notice of Allowance and Fees Due (PTOL-85)) dated Jun. 30, 2023 for U.S. Appl. No. 17/072,498 (pp. 1-7).
Office Action for Australian Application 2022203652 dated Jun. 23, 2023; 5 pps.
Office Action for Australian Application 2022203652 dated Oct. 20, 2023; 7 pps.
Office Action for Canadian Application 3021989 dated May 18, 2023; 3 pps.
Office Action for Chinese Application 201880087016.7 dated Jun. 15, 2022; 10 pps.
Office Action for European Patent Application 18877931.8 dated May 23, 2023; 4 pps.
Office Action for Indian Patent Application 201827038286 dated Jun. 8, 2021; 6 pps.
Office Action for Indian Patent Application 202027021653 dated May 6, 2022; 5 pps.
Office Action for Korean Patent Application 10-2018-7003178 dated Feb. 20, 2023; 2 pps.
Office Action for Korean Patent Application 10-2020-7017317 dated Aug. 1, 2023; 2 pps.
Office Action for Mexican Patent Application MX/a/2017/008000 dated Apr. 26, 2022; 6 pps.
Office Action for Mexican Patent Application MX/a/2018/000257 dated Mar. 2, 2022; 4 pps.
Office Action for Mexican Patent Application MX/a/2018/012967 dated Nov. 1, 2022; 3 pps.
Office Action for U.S. Appl. No. 14/575,635 dated Mar. 3, 2017; 25 pps.
Office Action for U.S. Appl. No. 14/575,635 dated Oct. 9, 2018; 16 pps.
Office Action for U.S. Appl. No. 15/741,009 dated Oct. 2, 2019; 6 pps.
Office Action for U.S. Appl. No. 15/741,011 dated Oct. 2, 2019; 7 pps.
Office Action for U.S. Appl. No. 17/072,498 dated Feb. 7, 2023; 9 pps.
Written Opinion for PCT/US23/25123 dated Sep. 29, 2023; 9 pps.
Written Opinion for PCT/IB2015/002531 dated Jun. 23, 2016; 6 pps.
Written Opinion for PCT/IB2016/001026 dated Jan. 5, 2017; 5 pps.
Written Opinion for PCT/IB2016/001027 dated Jan. 5, 2017; 5 pps.
International Search Report for PCT/US18/61696 dated Mar. 7, 2019; 2 pps.
Written Opinion or PCT/US18/61696 dated Mar. 7, 2019; 3 pps.
Office Action for U.S. Appl. No. 15/741,011 dated Oct. 2, 2019; 8pps.
Notice of Grant for 16774977.9 dated Mar. 12, 2020; 2 pps.
Syrette "https://en.wikipedia.org/wiki/Syrette" download date: Apr. 23, 2020; 2 pps.
Office Action for U.S. Appl. No. 15/741,012 dated Oct. 2, 2019; 7pps.
International Search Report for PCT/US2019/038302 dated Dec. 19, 2019; 2 pps.
Written Opinion or PCT/US2019/038302 dated Dec. 19, 2019; 4pps.
Written Opinion for WO 2016097872 dated May 6, 2016; 2 pps.
International Search Report for WO 2016097872 dated May 9, 1 pps.
Written Opinion for PCT/IB216/001042 dated Dec. 20, 2016; 6 pps.
Written Opinion for PCT/IB2016/001026 dated Nov. 7, 2016; 5 pps.
International Search Report or PCT/IB2016/001026 dated Nov. 8, 2016; 3 pps.
Written Opinion for PCT/IB2016/001027 dated Nov. 2, 2016; 5 pps.
International Search Report for PCT/IB2016/001027 dated Jan. 5, 2017; 2 pps.
Written Opinion for PCT/IB2016/001033 dated Dec. 7, 2016; 6 pps.

(56) References Cited

OTHER PUBLICATIONS

Written Opinion for PCT/IB2016/001050 dated Nov. 14, 2016; 5 pps.
International Search Report for PCT/IB2016/001050 dated Nov. 15, 2016; 2 pps.
Written Opinion for PCT/IIB2016/001034 dated Dec. 9, 2016; 6 pps.
Examination Report for PCT/IB2015/002531 dated May 28, 2020; 5 pps.
International Preliminary Report on Patentability for PCT/US18/61696 dated May 28, 2020; 4pps.
Written Opinion for WO2017/187262 dated Sep. 1, 2017; 7 pps.
International Search Report for WO2017/187262 dated Nov. 2, 2017; 3 pps.
Extended European Search Report (EESR) for European Patent Application No. 21907935.7 mailed on Sep. 23, 2024 (7 pages).
Notice of Allowance/Intention to Grant for Canadian Patent Application No. 3,021,989 mailed on Oct. 15, 2024 (1 page).
International Search Report for PCT/US24/14394 dated Jul. 29, 2024; 6 pps.
Notice of Allowance dated Jul. 17, 2024 for U.S. Appl. No. 29/736,603 (pp. 1-8).
Office Action (Non-Final Rejection) dated Aug. 28, 2024 for U.S. Appl. No. 18/181,664 (pp. 1-6).
Office Action (Notice of Allowance and Fees Due (PTOL-85)) dated Apr. 24, 2024 for U.S. Appl. No. 17/849,780 (pp. 1-7).
Office Action (Notice of Allowance and Fees Due (PTOL-85)) dated May 23, 2024 for U.S. Appl. No. 17/849,780 (pp. 1-3).
Office Action (Notice of Allowance and Fees Due (PTOL-85)) dated Jul. 15, 2024 for U.S. Appl. No. 17/849,780 (pp. 1-3).
Office Action for U.S. Appl. No. 18/181,664 dated Aug. 28, 2024; 6 pps.
Refresh Classic Lubricant Eye Drops, first available May 21, 2007, amazon.com, [online], [site visited Jul. 8, 2024], Available from internet URL: https://www.amazon.com/dp/B000R2VCIA (Year: 2007).
Written Opinion for PCT/US24/14394 dated Jul. 29, 2024; 10 pps.
Office Action (Notice of Allowance and Fees Due (PTOL-85)) dated Feb. 20, 2025 for U.S. Appl. No. 18/181,664; 7 pgs.
Communication pursuant to Article 94(3) EPC (Office Action) for EP 17730256.9 dated Jan. 23, 2025 (7 pgs.).
Notice of Allowance for U.S. Appl. No. 18/181,664 mailed on Feb. 20, 2025 (7 pgs.).
Summons to Attend Oral Proceedings (Rule 115(1) EPC) for European Patent Application 18877931.8 dated May 23, 2025; 7 pgs.
Office Action for U.S. Appl. No. 17/960,111 dated Jul. 2, 2025; 11 pps.
Office Action for U.S. Appl. No. 18/055,103 mailed on Jul. 30, 2025 (19 pages).
Communication pursuant to Rules 70(2) and 70a(2) EPC for European Patent Application No. 23824485.9 mailed on Sep. 9, 2025 (1 page).
Extended European Search Report (EESR) for European Patent Application No. 23824485.9 mailed on Aug. 22, 2025 (9 pages).
Communication pursuant to Rules 161(1) and 162 EPC for European Patent Application No. 24712355.7 mailed on Sep. 16, 2025 (3 pages).

* cited by examiner

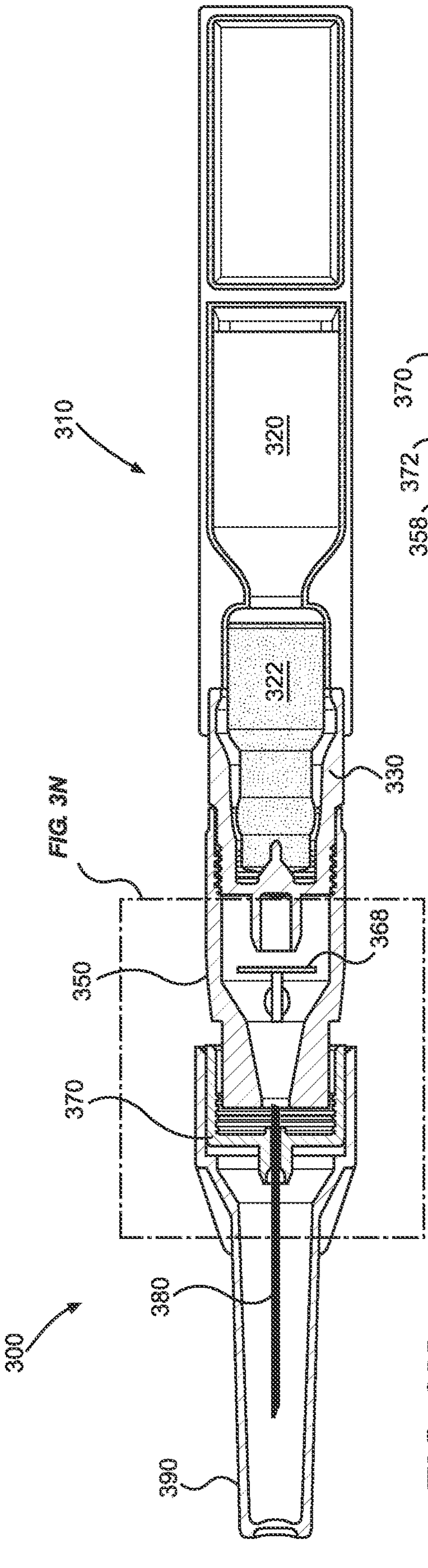
FIG. 3M
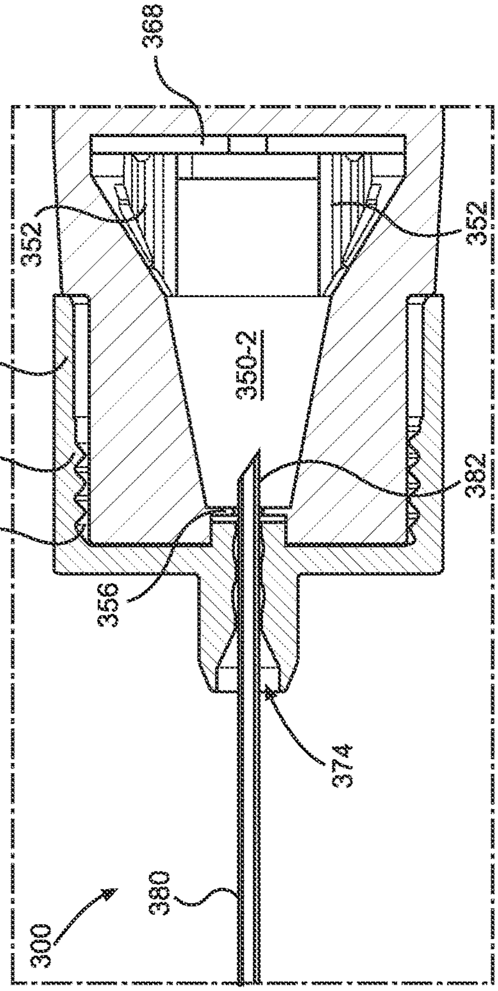
NFIG. 3N

SYSTEMS AND METHODS FOR PRE-FILLED DUAL-CHAMBER MEDICAL AGENT DELIVERY

CROSS-REFERENCE TO RELATED APPLICATIONS

This application claims benefit and priority (i) under 35 U.S.C. § 119(e) to, and is a Non-provisional of, U.S. Provisional Patent Application No. 63/076,968 filed on Sep. 11, 2020 and titled "PRE-FILLED DUAL-CHAMBER MEDICAL DELIVERY ASSEMBLIES", and (ii) under 35 U.S.C. § 120 to, and is a Continuation-in-Part (CiP) of, International Patent Application No. PCT/US2019/038302 filed on Jun. 20, 2019 and titled "SYSTEMS AND METHODS FOR DUAL-COMPONENT DRUG AGENT DELIVERY", which itself claims benefit and priority to U.S. Provisional Patent Application No. 62/687,340 filed on Jun. 20, 2018 and titled "DUAL CHAMBER BFS DRUG DELIVERY SYSTEM". Each of these above-referenced applications of which is hereby incorporated by reference herein in its entirety.

BACKGROUND

Every year, millions of people become infected and die from a variety of diseases, some of which are vaccine-preventable. Although vaccination has led to a dramatic decline in the number of cases of several infectious diseases, some of these diseases remain quite common. In many instances, large populations of the world, particularly in developing countries, suffer from the spread of vaccine-preventable diseases due to ineffective immunization programs, either because of poor implementation, lack of affordable vaccines, or inadequate devices for administering vaccines, or combinations thereof.

Some implementations of immunization programs generally include administration of vaccines via a typical reusable syringe. However, in many situations, particularly in developing countries, the administration of vaccines occur outside of a hospital and may be provided by a non-professional, such that injections are given to patients without carefully controlling access to syringes. The use of reusable syringes under those circumstances increases the risk of infection and spread of blood-borne diseases, particularly when syringes, which have been previously used and are no longer sterile, are used to administer subsequent injections. For example, the World Health Organization (WHO) estimates that blood-borne diseases, such as Hepatitis and human immunodeficiency virus (HIV), are being transmitted due to reuse of such syringes, resulting the death of more than one million people each year.

Previous attempts at providing single-use or disposable injection devices to remedy such problems in the industry have achieved measurable success but have failed to adequately remedy the existing problems. Pre-filled, single-use injection devices manufactured via injection molding or Form-Fill-Seal (FFS) processes, such as the Uniject™ device available from the Becton, Dickinson and Company of Franklin Lakes, NJ, for example, while offering precise manufacturing tolerances in the range of two thousandths of an inch (0.002-in; 50.8 μm) to four thousandths of an inch (0.004-in; 101.6 μm)—for hole diameters in molded parts, require separate sterilization processes (e.g., gamma radiation) that are not compatible with certain fluids, provide production rates limited to, for example, approximately nine thousand (9,000) non-sterile units per hour.

BRIEF DESCRIPTION OF THE DRAWINGS

An understanding of embodiments described herein and many of the attendant advantages thereof may be readily obtained by reference to the following detailed description when considered with the accompanying drawings, wherein:

FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V are various views of a pre-filled dual-chamber medical agent delivery system according to some embodiments;

DETAILED DESCRIPTION

I. Introduction

Embodiments of the present invention provide systems and methods for pre-filled, single-dose, and/or dual-chamber medical agent delivery that overcome drawbacks of current delivery devices and methods. For example, the pre-filled, single-dose, and/or dual-chamber medical delivery systems or assemblies of some embodiments may include a plastic (e.g., a Blow-Fill-Seal (BFS)) vial or bottle coupled to a specialized collar, coupling, or connector that facilitates coupling of an administration member (e.g., a needle/canula) to the BFS vial. In some embodiments, such a pre-filled, single-dose, and/or dual-chamber medical delivery assembly may be selectively actuated by application of rotational force to a cap covering the administration member, causing the administration member to axially advance and pierce a fluid reservoir of the BFS vial. In some embodiments, a specialized BFS coupling, connector, or collar may be snapped onto a BFS vial, thereby puncturing the BFS vial. According to some embodiments, a modular chamber element (e.g., a mixing chamber) may be coupled to the BFS collar such that a medicament and/or agent stored or housed in the modular chamber may be activated, diluted, reconstituted, etc., when introduced to fluid flow from the BFS vial via the BFS collar/connector. Utilization of such systems that employ BFS vials, BFS connectors, and/or modular mixing chambers may be advantageous and may address various shortcomings of previous systems.

BFS modules may, for example, offer a less expensive alternative to typical vials or devices created via other manufacturing techniques. In some embodiments, BFS modules (e.g., due to the nature of the BFS manufacturing process) may not require separate sterilization (e.g., and may accordingly be compatible with a wider array of fluids), may provide enhanced production rates of, for example, approximately thirty thousand (30,000) sterile/aseptic units per hour, and/or may be provided to an end-user for a smaller per dose/unit cost than other manufacturing techniques. In some embodiments, these advantages may come with an attendant drawbacks of reduced manufacturing tolerances and other disadvantages of utilizing a "soft" plastic (e.g., having a Shore/Durometer "OO" hardness of between 60 and 70 and/or a Shore/Durometer "A" hardness between 20 and 50). BFS processes may, for example, offer less precise manufacturing tolerances in the range of five hundredths of an inch (0.05-in; 1.27 mm) to fifteen hundredths of an inch (0.15-in; 3.81 mm)—for linear dimensions, e.g., in accordance with the standard ISO 2768-1 "General tolerances for linear and angular dimensions without individual tolerance indications" published by the International Organization for Standardization (ISO) of Geneva, Switzerland (Nov. 15, 1989).

II. Pre-filled Dual-Chamber Medical Agent Delivery Systems

Figure 1A:
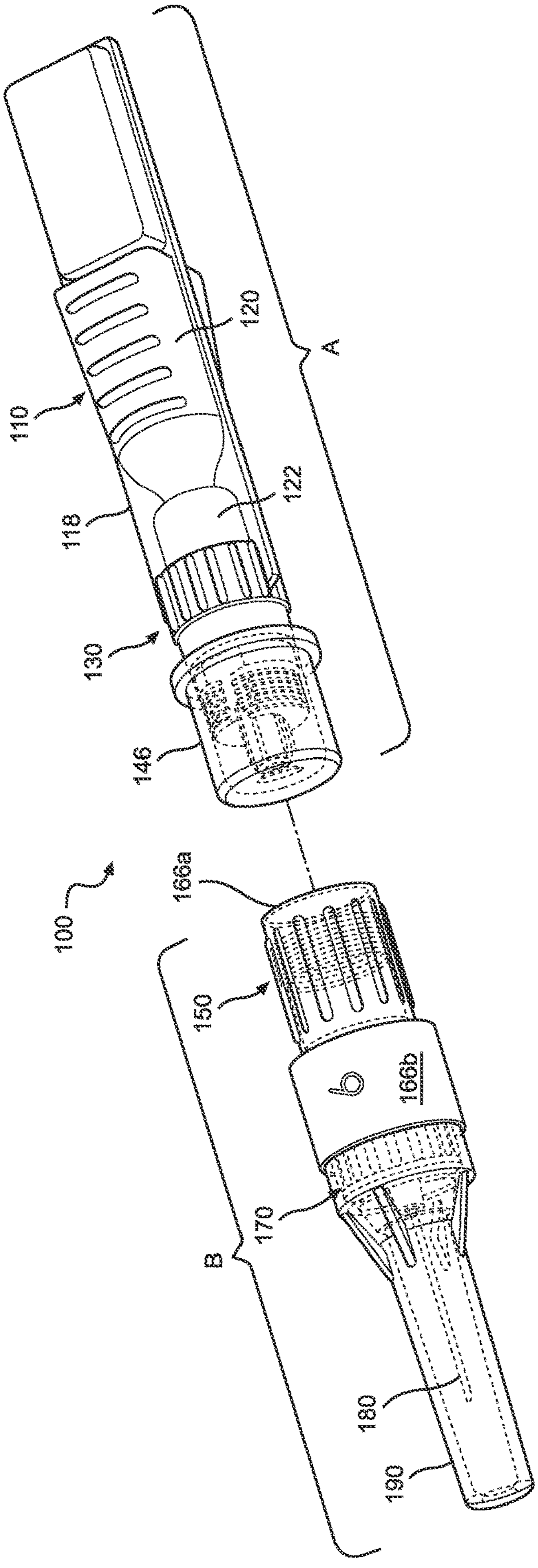
FIG. 1A and FIG. 1B are perspective and side cross-section views of a pre-filled dual-chamber medical agent delivery system according to some embodiments.
Figure 1B:
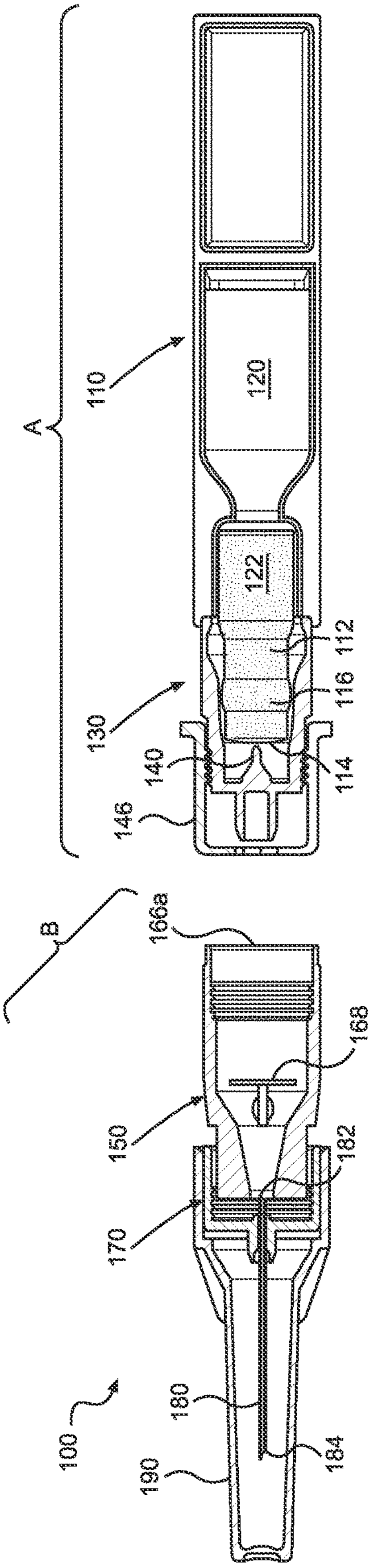

Referring initially to FIG. 1A and FIG. 1B, perspective and side cross-section views of a pre-filled dual-chamber (and/or single-dose) medical agent delivery system 100 according to some embodiments are shown. In some embodiments, the pre-filled dual-chamber medical agent delivery system 100 may comprise various inter-connected and/or modular components such as a BFS vial 110 comprising and/or defining a vial neck 112, a fluid seal 114, a mounting flange 116, a bottle flange 118, a collapsible reservoir 120, and/or a dispensing reservoir 122. In some embodiments, the BFS vial 110 and/or a portion thereof may be referred to as a "first chamber" (e.g., containing a first fluid—not explicitly shown or labeled). According to some embodiments, the BFS vial 110 may comprise a plastic and/or synthetic vial that is constructed via any practicable manufacturing techniques. In some embodiments the BFS manufacturing technique may be utilized. According to some embodiments, the pre-filled dual-chamber medical agent delivery system 100 may comprise a mounting collar or connector 130 (e.g., comprising a piercing element 140), a collar or connector cap 146, a modular chamber element 150 comprising one or more seals 166*a-b* protecting a substrate 168 housed and/or stored within the modular chamber element 150, a housing 170 that couples to and/or houses an administration member 180, and/or a cap 190. In some embodiments, the modular chamber element 150 may be referred to as a "second chamber" or "mixing chamber". According to some embodiments, the pre-filled dual-chamber medical agent delivery system 100 may include a modular design consisting of separately constructed components 110, 130, 150, 170, 190 cooperatively arranged and coupled to one another. According to some embodiments, some of the components 110, 130, 150, 170, 190 may be manufactured, created, molded, and/or otherwise formed together. The modular chamber element 150, the housing 170, and/or the connector 130 may, for example, be integrally constructed to form fewer separate pierces than are depicted.

In some embodiments, the collapsible reservoir 120 may be filled (fully or partially) with a fluid or other agent (not separately shown) such as a diluent. According to some embodiments, the fluid may be injected into the BFS vial 110 in a sterile environment during manufacture via a BFS process and sealed within the BFS vial 110 via the fluid seal 114. The fluid seal 114 may comprise a portion of the molded BFS vial 110 for example that is configured to be pierced to expel the fluid, e.g., such as by providing a flat or planar piercing surface and/or by being oriented normal to an axis of the BFS vial 110 (and/or the pre-filled dual-chamber medical agent delivery system 100). In some embodiments, the fluid seal 114 may comprise a foil, wax, paper, and/or other thin, pierceable object or layer coupled to the BFS vial 110. In some embodiments, the neck 112 of the BFS vial 110 may comprise the mounting flange 116 such as, e.g., the "doughnut"-shaped exterior flange depicted (and/or one or more other tabs, detents, protrusions, and/or other features). According to some embodiments, and as depicted, the neck 112 may be cylindrically shaped. In some embodiments, the neck 112 may comprise one or more other cross-sectional shapes or configurations such as a triangle, square, rectangle, pentagon, hexagon, star, and/or octagon shape. In some embodiments, the shape of the neck 112 may correspond to a type of fluid agent stored in the BFS vial 110. According to some embodiments, the stored fluid agent may generally pass between the collapsible reservoir 120 and the connected dispensing reservoir 122. In some embodiments, a juncture, constriction, valve, and/or passage (not separately labeled) between the dispensing reservoir 122 and the collapsible reservoir 120 may restrict flow such that the fluid may readily enter the dispensing reservoir 122 but may not readily return to the collapsible reservoir 120.

According to some embodiments, the connector 130 may be axially engaged to couple with the BFS vial 110 via application of a mating axial force. The connector 130 may be urged onto the neck 112 of the BFS vial 110, for example, such that it accepts and/or selectively couples to the mounting flange 116, thereby removably coupling the BFS vial 110 and the mounting collar 130. According to some embodiments, the connector 130 may be shaped to correspond to and/or cooperatively mate with the shape of the neck 112 of the BFS vial 110. In the case that the neck 112 is cylindrically or triangularly shaped, for example, the connector 130 may comprise a cylindrical or triangular opening and/or passage (not separately labeled in FIG. 1A or FIG. 1B), respectively. In some embodiments, uncoupling of the BFS vial 110 and the connector 130 may be mechanically prohibited. The mounting flange 116 may effectively lock into the connector 130 once inserted, for example, preventing or inhibiting removal thereafter. According to some embodiments, the connector 130 may engage with the bottle flange 118 (and/or portions thereof) such that rotation of the connector 130 with respect to the BFS vial 110 is restricted in the case that they are coupled.

In some embodiments, the BFS vial 110 may be engaged with the connector 130 in two positions or stages. In a first stage or position (e.g., a transport and/or storage stage or position) as depicted in FIG. 1A and FIG. 1B, for example, the BFS vial 110 may be partially inserted into the connector 130 such that the fluid seal 114 is positioned adjacent to (e.g., axially) and/or aligned with the piercing element 140. In a second stage or position (not shown; e.g., an activation stage or position), the BFS vial 110 may be fully inserted into the connector 130 such that the piercing element 140 pierces the fluid seal 114 and/or such that the mounting flange 116 is retained by the connector 130. According to some embodiments, such as in the case that the BFS vial 110 and the connector 130 are engaged in the first position, a distal end of the connector 130 may be covered by the connector cap 146 (e.g., to maintain sterility of some or all portions of the connector 130).

In some embodiments, the modular chamber element 150 may be selectively coupled to the distal end of the connector 130, e.g., via a threaded connection as depicted, and upon removal of the connector cap 146 and a first or end seal 166*a* of the modular chamber element 150. According to some embodiments, the modular chamber element 150 may be coupled to the housing 170 such as via a threaded connection as shown. In some embodiments, the connection between the housing 170 (and the cap 190) and the modular chamber element 150 may be protected and/or sealed via a second or external (e.g., shrink wrap) seal 166*b*. According to some embodiments the housing 170 may couple to and/or retain the administration member 180. The administration member 180 may be inserted into the housing 170, for example, such that a first or piercing end 182 is disposed within the housing 170 and/or extending into the modular chamber element 150, e.g., in the case that the modular chamber element 150 is coupled to the housing 170, and a second or administration end 184 extends axially distal from the BFS vial 110. In some embodiments, the administration end 184 and/or a distal portion of the administration member 180 may be housed, shrouded, and/or covered by the cap 190. According to some embodiments, the cap 190 may be configured to house the administration member 180 and to removably couple to the housing 170 (e.g., by fitting over an external portion thereof).

According to some embodiments, the housing 170 and cap 190 combination may be utilized to couple and/or mate the administration member 180 with the modular chamber element 150. In some embodiments, the modular chamber element 150 may be coupled to the connector 130 to provide a mechanism via which the administration member 180 may be coupled to be in fluid communication with the soft plastic BFS vial 110 in a reliable manner. Due to the nature of the BFS plastic and/or process and/or the small form-factor of the BFS vial 110, for example, providing external machine-type threads (not shown) directly on the neck 112 would not be a viable option for it would result in an imprecise, unreliable, and/or non-water tight coupling (i.e., the threads would be deformable even if they could be properly manufactured to within the desired tolerances, which itself is not a likely result) between he BFS vial 110 and, e.g., the connector 130, the modular chamber element 150, and/or the housing 170.

In some embodiments, the administration member 180 may include a needle or canula for at least one of subcutaneous, intramuscular, intradermal, and intravenous injection of a combination of the fluid agent from the BFS vial 110 and the substrate 168 (and/or an agent deposited, injected, and/or formed or printed thereon; e.g., a combined agent) into the patient. For ease of explanation and description, the figures and the description herein generally refer to the administration member 180 as a needle. However, it should be noted that, in other embodiments, the administration member 180 may include a nozzle (not shown) configured to control administration of the combined agent to the patient. The nozzle may include a spray nozzle, for example, configured to facilitate dispersion of the combined agent into a spray. Accordingly, a housing 170 fitted with a spray nozzle may be particularly useful in the administration of a combined agent into the nasal passage, for example, or other parts of the body that benefit from a spray application (e.g., ear canal, other orifices). In other embodiments, the nozzle may be configured to facilitate formation of droplets of the combined fluid agent. Thus, a housing 170 including a droplet nozzle may be useful in the administration of a combined agent by way of droplets, such as administration to the eyes, topical administration, and the like.

As generally understood, the combined agent or drug may include any type of combined agent to be injected into a patient (e.g., mammal, either human or non-human) and capable of producing an effect (alone, or in combination with an active ingredient). Accordingly, the combined agent may include, but is not limited to, a vaccine, a drug, a therapeutic agent, a medicament, a diluent, and/or the like. In some embodiments, the substrate 168 may comprise, for example, the active ingredient of the drug agent (i.e., the second component or substance thereof) or an object that retains, carries, or holds the active ingredient. According to some embodiments, the substrate 168 may be disposed in the modular chamber element 150 (e.g., during the manufacturing process) and/or may be configured in various shapes (e.g., disk, spiral, sphere, tablet), e.g., to promote interaction of the fluid agent with the active ingredient. In some embodiments, the substrate 168 may comprise an inactive object such as a bag, pouch, capsule, paper disk, and/or tablet that contains the second component or substance (e.g., the active ingredient). The second component or substance may, for example, be disposed in a powdered, dry, granulated, dehydrated, lyophilized, cryodesiccated, desiccated, powdered, and/or solid form and may be stored in or on the substrate 168.

In some embodiments, the second component or substance may be disposed in a solid and/or compressed shape such as a pill, cake, tablet (e.g., an annular-shaped tablet), a fine powder, and/or in aerated form. In some embodiments, the second component or substance may be combined or mixed with other substances (e.g., inactive and/or non-reactive substances) such as by being combined with large molecule sugars, thickeners, etc. According to some embodiments, the modular chamber element 150 may comprise or define a void, channel, projection, groove, track, diffuser, or other feature (not shown) that may house or retain the substrate 168 and/or the active ingredient. In some embodiments, the substrate 168 may not comprise a separate object from the active ingredient but may be representative of a disposing of the second component or substance in the modular chamber element 150. The second component or substance may, for example, be directly deposited (e.g., sprayed and/or printed) on the inside surface of the modular chamber element 150, e.g., in one or more patterns such as a spiral (e.g., rifle) pattern. According to some embodiments, the inside surface of the modular chamber element 150 (or a portion thereof) may be coated with the second component or substance (or a mixture containing or carrying the second component or substance). In some embodiments, the printing or depositing may be conducted in a manner that increases the surface are of the second component or substance exposed to the fluid agent flow (e.g., a raised criss-cross pattern, raised rifling ridges). An increased surface area of contact between the second component or substance and the fluid agent (or other first component or substance) may, for example, increase dissolution of the second component or substance and/or reduce an amount of time required for a desired dissolution level. Various different parameters for the dimension, shape, thickness, and/or dosage of the active ingredient may be selected for different types of active ingredients, the parameter values selected to meet certain goals. Examples of such goals may include, without limitation: (i) maximizing the surface area of the second component or substance; (ii) minimizing the dissolution time; (iii) maximizing the percentage of the second component or substance that is dissolved (e.g., within a certain amount of time and/or given a certain amount or type of diluent); and (iv) a desired concentration of the resulting drug agent (e.g., a desired curve of concentration range). For example, in some embodiments the amount, pattern or configuration of the second component or substance may be designed such that ninety percent (90%) of the second component or substance (and/or active ingredient) is dissolved in a particular first component or substance (e.g., fluid agent) within five to six (5-6) seconds of the first component or substance being released into the modular chamber element 150 from the BFS vial 110.

According to some embodiment, either or both of the combined agent and the active ingredient (i.e., the drug agent and/or components thereof) may be tracked, monitored, checked for compatibility with each other, etc., such as by utilization of electronic data storage devices (not shown) coupled to the various modules or components such as the BFS vial 110, the modular chamber element 150, the housing 170, and/or the connector 130.

According to some embodiments, the connector 130, the modular chamber element 150, the housing 170, and/or the cap 190 may be composed of a medical grade material. In some embodiments, the connector 130, the modular chamber element 150, the housing 170, and/or the cap 190, may be composed of a thermoplastic polymer or other "hard" plastic (e.g., greater than 80 on the Rockwell "R" scale), including, but not limited to, polybenzimidazole, acrylonitrile butadiene styrene (ABS), polystyrene, polyvinyl chloride, or the like.

In some embodiments, the pre-filled dual-chamber medical agent delivery system 100 may be advantageously manufactured (in mass quantities), assembled, and/or provided in separate parts or portions, namely, at least the BFS vial 110, connector 130, and connector cap 146 portion (e.g., a "first" piece such as a BFS module or assembly; labeled "A" in FIG. 1A and FIG. 1B) and the connector 130, modular chamber element 150, housing 170 (with the administration member 180), and cap 190 portion (e.g., a "second" piece such as an administration module or assembly; labeled "B" in FIG. 1A and FIG. 1B), with such different plastic parts/portions being selectively coupled to administer a medication (e.g., a combined medical agent) to a patient. In practice, for example, some or all of the following procedures may be followed to utilize the pre-filled dual-chamber medical agent delivery system 100 to administer a combined medication to a patient. In some embodiments, an area of injection may be cleaned and/or otherwise prepared. According to some embodiments, the first part "A" (e.g., the BFS module or assembly) may be activated by application of axial force that forces the BFS vial 110 from the first and partially-engaged mating position with the connector 130 to the second and fully-engaged mating position, whereby the piercing element 140 pierces the fluid seal 114. In such a manner, for example, the connector 130 may "click" or snap onto the BFS vial 110 to activate the BFS module/assembly. In some embodiments, the connector cap 146 may then be removed. According to some embodiments, the first seal 166*a* may be removed from the second part "B" (e.g., from the administration module/assembly and/or from the modular chamber element 150 thereof) and the second part "B" may be axially aligned with the first part "A" and coupled thereto. The modular chamber element 150 may be threaded onto the connector 130, for example, joining the two parts "A" and "B". In some embodiments, the collapsible reservoir 120 may then be squeezed (e.g., radially inward force may be applied) to force the fluid through the connector 130 and into the modular chamber element 150 such that it comes in contact with, mixes with, dissolves, reconstitutes, and/or otherwise activates any desired ingredient on the substrate 168, thereby creating the combined agent. In some embodiments, the pre-filled dual-chamber medical agent delivery system 100 may be shaken to more fully and/or more quickly introduce the fluid and the substrate (and/or any substance thereof).

According to some embodiments, the housing 170 may, as a component of a pre-packaged second part "B" (e.g., the administration module/assembly) for example, be only partially engaged with the modular chamber element 150. Only a portion of the threads may be engaged, for example, such that the second part "B" is at least loosely coupled as a single object assembly but the administration member 180 is not advanced axially enough to pierce the modular chamber element 150. In such a manner, for example, a user may couple the first and second parts "A" and "B" and then selectively engage the administration member 180 to puncture the modular chamber element 150 (e.g., thereby exposing the combined agent to the administration member 180).

In some embodiments, the user may hold the connector 130 and/or the modular chamber element 150 with one hand/fingers and thread (e.g., continue threading) the housing 170 (e.g., coupled to the administration member 180 and cap 190) fully into/onto the modular chamber element 150 by applying rotational force to the cap 190. The cap 190 may comprise one or more internal keys (not shown) that engage with one or more features of the housing 170 to transfer the rotational force to the housing 170 and accordingly advance the mating of the threads between the housing 170 and the modular chamber element 150. As the threading/mating advances the first or piercing end 182 of the administration member 180 may be axially advanced to pierce the modular chamber element 150, thereby completing the activation of the pre-filled dual-chamber medical agent delivery system 100.

According to some embodiments, the cap 190 may be removed to reveal the administration member 180 and/or the administration end 184 thereof. In some embodiments, the administration member 180 (e.g., the administration end 184 thereof) may be inserted into (and/or otherwise engaged with) the patient and the collapsible reservoir 120 may be squeezed (e.g., receive an application of radially inward force), thereby expelling the combined agent through the administration member 180 and into the patient. In some embodiments, the administration member 180 may be withdrawn from the patient and/or the pre-filled dual-chamber medical agent delivery system 100 may be properly disposed of. While the connector 130, the housing, 170, and the modular chamber element 150 are depicted as separate couplable objects, in some embodiments they may be manufactured (e.g., molded) as a single object or piece or may comprise additional pieces or parts. Similarly, while the cap 190 is depicted as a separate component, in some embodiments the cap 190 may be integral to (e.g., comprise a portion of) one or more of the connector 130, the housing, 170, and the modular chamber element 150.

In some embodiments, fewer or more components 110, 112, 114, 116, 118, 120, 122, 130, 140, 146, 150, 166*a-b*, 168, 170, 180, 182, 184, 190 and/or various configurations of the depicted components 110, 112, 114, 116, 118, 120, 122, 130, 140, 146, 150, 166*a-b*, 168, 170, 180, 182, 184, 190 may be included in the pre-filled dual-chamber medical agent delivery system 100 without deviating from the scope of embodiments described herein. In some embodiments, the components 110, 112, 114, 116, 118, 120, 122, 130, 140, 146, 150, 166*a-b*, 168, 170, 180, 182, 184, 190 may be similar in configuration and/or functionality to similarly named and/or numbered components as described herein. In some embodiments, the pre-filled dual-chamber medical agent delivery system 100 (and/or portions thereof) may comprise a disposable, single-dose delivery assembly operable to be utilized to execute, conduct, and/or facilitate the method 600 of FIG. 6 herein, and/or portions thereof.

Figure 2:
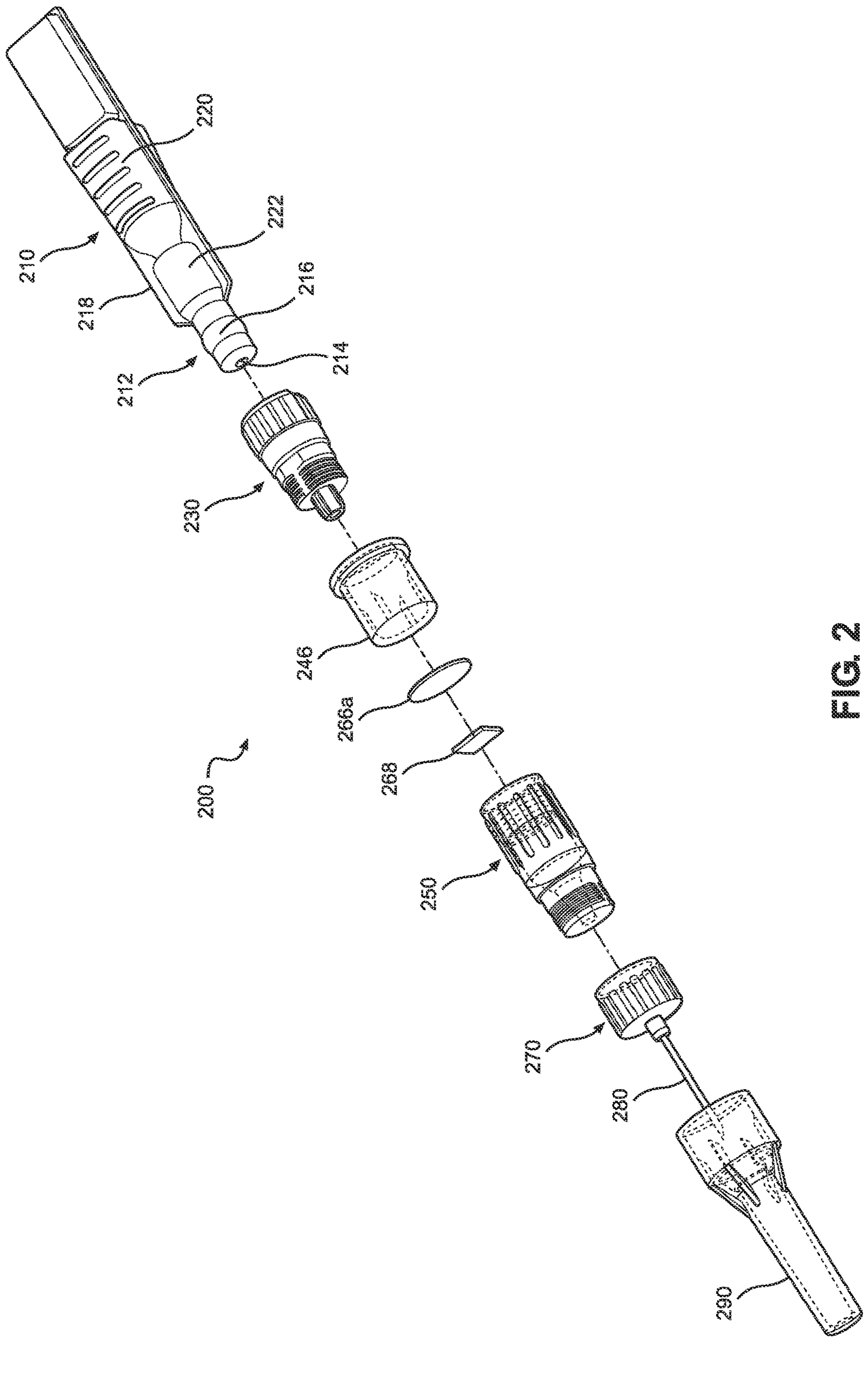
FIG. 2 is a perspective assembly view of a pre-filled dual-chamber medical agent delivery system according to some embodiments.

Turning to FIG. 2, a perspective assembly view of a pre-filled dual-chamber medical agent delivery system 200 according to some embodiments is shown. In some embodiments, the pre-filled dual-chamber medical agent delivery system 200 may be similar in configuration to the pre-filled dual-chamber medical agent delivery system 100 of FIG. 1A and FIG. 1B herein. According to some embodiments, the pre-filled dual-chamber medical agent delivery system 200 may comprise a mass-produced single-dose vaccine and/or other medical treatment delivery device and/or assembly. The pre-filled dual-chamber medical agent delivery system 200 may comprise, for example, a plastic bottle 210 comprising a neck portion 212 with a fluid seal 214 at an end of the neck portion 212. In some embodiments, the neck portion 212 may comprise a mounting feature 216 such as the exterior rounded flange, collar, track, ferrule, and/or ring shown in FIG. 2. According to some embodiments, particularly in the case that the plastic bottle 210 is formed from two sheets of molded plastic base material, the plastic bottle 210 may comprise and/or define a side flange 218. In some embodiments, the plastic bottle 210 may comprise and/or define one or more of a first reservoir 220 and a second reservoir 222. The plastic bottle 210 may comprise, for example, a BFS bottle formed with two distinct reservoirs 220, 222 that are in fluid communication with each other. In some embodiments, one or more fluids (not shown) injected into the plastic bottle 210 (e.g., during manufacture in the case that BFS processes are utilized) may be stored within one or more of the reservoirs 220, 222. According to some embodiments, the neck portion 212 may define an interior volume and/or passage (not separately shown) that is in fluid communication with the reservoirs 220, 222. In such a manner, for example, the fluid seal 214 may retain the one or more fluids within the combined volume of the neck portion 212, the first reservoir 220, and the second reservoir 222.

In some embodiments, the combined volume of the neck portion 212, the first reservoir 220, and the second reservoir 222 may be partially filled with a first fluid such as a liquid diluent and/or first medical agent and partially filled with a second fluid such as a gas (e.g., air). According to some embodiments, at least the first reservoir 220 may be compressible by application of human-applied radial inward force (e.g., a squeezing). In some embodiments, the second reservoir 222 may comprise a cylindrical shape such as to provide a uniform side-view surface to facilitate inspection of any fluid stored therein.

According to some embodiments, the pre-filled dual-chamber medical agent delivery system 200 may comprise an adapter 230 (which may selectively be covered by and/or coupled to a transport cap 256) that serves as a joining element between the plastic bottle 210 and a mixing chamber 250 and/or that is operable to selectively puncture the fluid seal 214. The adapter 230 may be engaged with the plastic bottle 210 by snapping onto the mounting feature 216, for example, and may thereby cause the fluid seal 214 to be broken (e.g., by one or more features disposed within the adapter 230; not shown). In some embodiments, the combined volume of the neck portion 212, the first reservoir 220, the second reservoir 222, and an interior volume (not shown) of the adapter 230 may comprise and/or define a "first chamber"—e.g., in which the first and/or second fluids are retained.

In some embodiments, the transport cap 246 may be removed (and discarded), exposing the end of the adapter 230 and/or providing fluid access to the first chamber. According to some embodiments, a seal 266*a* of the mixing chamber 250 may be removed (and discarded) to reveal and/or expose an interior volume (not separately labeled) of the mixing chamber 250 and the mixing chamber 250 and the adapter 230 may be engaged and coupled together. In some embodiments, such coupling may be effectuated utilizing threads, tabs, slots, and/or other mating features, joints, and/or objects. In some embodiments, the mixing chamber 250 may comprise and/or define a "second chamber"—e.g., in which a dry ingredient and/or agent 268 is retained or housed. The dry agent 268 may comprise, for example, a lyophilized or freeze-dried agent deposited on a substrate and/or carrier mechanism that is disposed within the mixing chamber 250. According to some embodiments, once coupled, the combined volume of the neck portion 212, the first reservoir 220, the second reservoir 222, the adapter 230, and the mixing chamber 250 may be in fluid communication, allowing any fluid agent(s) from the reservoirs 220, 222 to pass into the mixing chamber 250 and interact with the dry agent 268. In some embodiments, the first reservoir 220 may be squeezed, thereby compressing any gaseous fluid therein and forcing any liquid in the combined volume to engage with the dry agent 268 in the mixing chamber 250. According to some embodiments, the mixing chamber 250 may be sealed at a distal end thereof such that the combined volume of the coupled components 210, 230, 250 remains enclosed. In some embodiments, a needle hub 270 comprising a canula 280 may be coupled to the mixing chamber 250, such as to pierce the seal (not separately labeled) of the mixing chamber 250 and release the combined fluid agent (e.g., the dry ingredient 268 and one or more fluids from the plastic bottle 210) through the canula 280 and into a target (not shown).

According to some embodiments, the needle hub 270 may be such coupled to the mixing chamber 250 utilizing threads, tabs, slots, and/or other mating features, joints, and/or objects. In some embodiments, an engagement and/or coupling of the needle hub 270 with the mixing chamber 250 may cause a piercing of the seal of the mixing chamber 250, thereby permitting the mixed, reconstituted, and/or otherwise combined agent (e.g., liquid, fluid, solution, and/or other effluent) from the combined volume of the two chambers to be expelled via the canula 280. In some embodiments, cap 290 may shield the canula 280, e.g., to prevent unintentional engagement of the canula 280. According to some embodiments, the cap 290 may be utilized to engage the needle hub 270 with the mixing chamber 250 and/or to pierce the seal of the mixing chamber 250. The cap 290 may be employed as a driver to couple the needle hub 270 with the mixing chamber 250, for example, and/or to advance the canula 280 through the seal of the mixing chamber 250 such that the canula 280 enters fluid communication with the combined volume of the coupled components 210, 230, 250.

In some embodiments, fewer or more components 210, 212, 214, 216, 218, 220, 222, 230, 246, 250, 266*a*, 268, 270, 280, 290 and/or various configurations of the depicted components 210, 212, 214, 216, 218, 220, 222, 230, 246, 250, 266*a*, 268, 270, 280, 290 may be included in the pre-filled dual-chamber medical agent delivery system 200 without deviating from the scope of embodiments described herein. In some embodiments, the components 210, 212,

214, 216, 218, 220, 222, 230, 246, 250, 266*a*, 268, 270, 280, 290 may be similar in configuration and/or functionality to similarly named and/or numbered components as described herein. In some embodiments, the pre-filled dual-chamber medical agent delivery system 200 (and/or portions thereof) may comprise a disposable, single-dose delivery assembly operable to be utilized to execute, conduct, and/or facilitate the method 600 of FIG. 6 herein, and/or portions thereof.

Referring additionally to FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V, various views of a pre-filled dual-chamber medical agent delivery system 300 according to some embodiments are shown. In some embodiments, the pre-filled dual-chamber medical agent delivery system 300 may utilize and/or employ a BFS vial 310 to safely, inexpensively, reliably, and/or conveniently administer a combined medicament to a patient or other target (not shown). The BFS vial 310 may comprise and/or define, for example, a vial neck 312, a fluid seal 314, a mounting flange 316, a wing flange 318, a collapsible reservoir 320, and/or a dispensing reservoir 322. In some embodiments, the collapsible reservoir 320 may be filled (fully or partially) with a fluid or other agent (not separately shown) such as a diluent or a first active ingredient (e.g., a single dose thereof). According to some embodiments, the fluid may be injected into the BFS vial 310 in a sterile environment during manufacture via a BFS process and sealed within the BFS vial 310 via the fluid seal 314. The fluid seal 314 may comprise a portion of the molded BFS vial 310 for example that is configured to be pierced to expel the fluid, e.g., such as by providing a flat or planar piercing surface and/or by being oriented normal to an axis of the BFS vial 310 (and/or the pre-filled dual-chamber medical agent delivery system 300). In some embodiments, the fluid seal 314 may comprise a foil, wax, paper, and/or other thin, pierceable object or layer coupled to (and/or integral to) the BFS vial 310. In some embodiments, the neck of the BFS vial 310 may comprise the mounting flange 316 such as, e.g., the "doughnut"-shaped rounded exterior flange depicted. According to some embodiments, the fluid may generally pass between the collapsible reservoir 320 and the connected dispensing reservoir 322. In some embodiments, a juncture, valve, constriction, and/or passage (not separately labeled) between the dispensing reservoir 322 and the collapsible reservoir 320 may restrict flow such that the fluid may readily enter the dispensing reservoir 322 but may not readily return to the collapsible reservoir 320.

According to some embodiments, a mounting collar 330 may be selectively coupled to the BFS vial 310. The mounting collar 330 may comprise, for example, one or more anti-rotation features 332 disposed at a first end thereof (and/or one or more frangible positioning elements 332-1), external threads 334 disposed at a second end thereof, a fluid outlet 336 defining a fluid outlet conduit 336-1, and/or a mounting recess 338. According to some embodiments, the mounting collar 330 may comprise and/or define a piercing element 340, and exterior flange 342, and/or may be covered and/or sealed by a collar cap 346 (e.g., covering at least the fluid outlet 336). In some embodiments, the mounting collar 330 may be axially engaged to couple with the BFS vial 310 via application of an axial mating or coupling force (e.g., a first axial force). The mounting collar 330 may be urged onto the neck 312 of the BFS vial 310, for example, such that the mounting recess 338 accepts and/or selectively couples to the mounting flange 316, thereby removably coupling the BFS vial 310 and the mounting collar 330. In some embodiments, uncoupling of the BFS vial 310 and the mounting collar 330 may be mechanically prohibited. According to some embodiments, the mounting collar 330 may engage with the wing flange 318 (and/or portions thereof) such that rotation of the mounting collar 330 with respect to the BFS vial 310 is restricted in the case that they are coupled. The mounting collar 330 may comprise, for example, the one or more anti-rotation features 332 that are oriented and/or configured to accept and/or couple to one or more respective wing flanges 318.

Figure 3A:
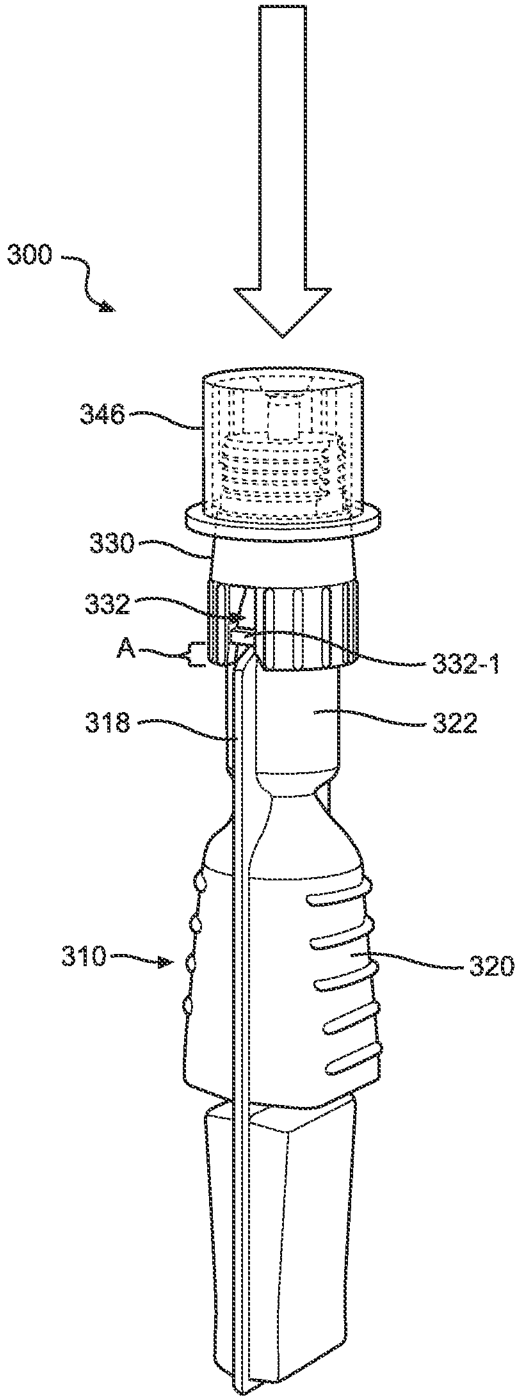
Figure 3B:
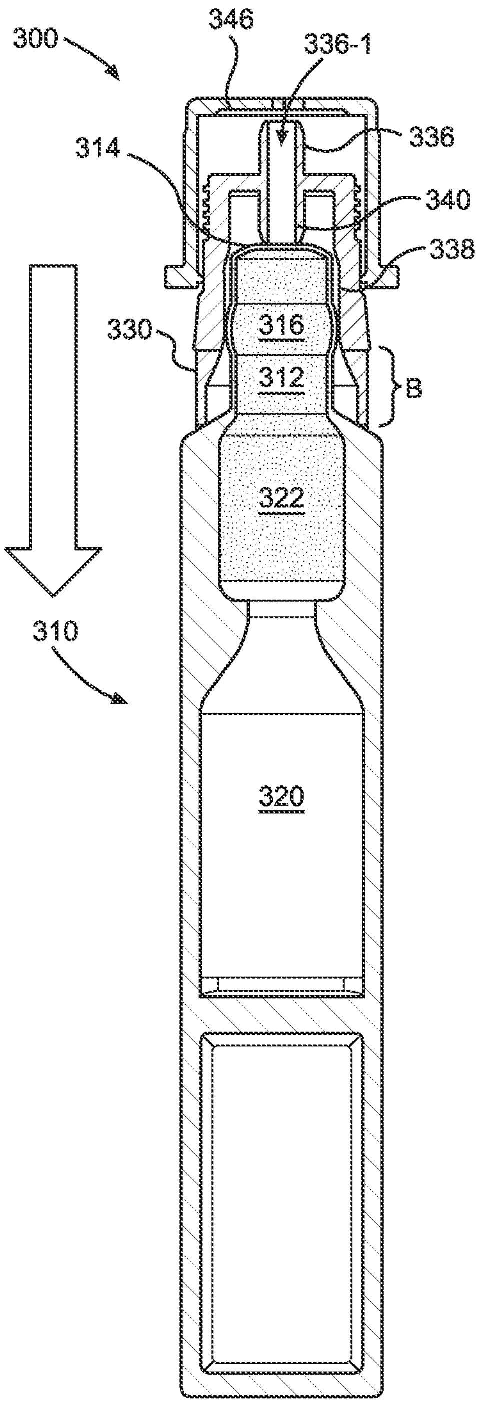

In some embodiments, the BFS vial 310 may be engaged with the mounting collar 330 in two positions or stages (e.g., corresponding to first and second states of the pre-filled dual-chamber medical agent delivery system 300). In a first stage or position (e.g., corresponding to the first state of the pre-filled dual-chamber medical agent delivery system 300) as depicted in FIG. 3A and FIG. 3B, for example, the BFS vial 310 may be partially inserted into the mounting collar 330 such that the fluid seal 314 is positioned adjacent to (e.g., axially) and/or aligned with the piercing element 340. According to some embodiments, attainment and/or maintenance of the first position may be facilitated by the frangible positioning elements 332-1. As depicted in FIG. 3A and FIG. 3B, for example, the BFS vial 310 may be inserted into the mounting collar 330 to an extent until the leading edges of the wing flanges 318 enter into the anti-rotation features 332 (e.g., axial slits, as depicted) and make contact with and/or are blocked by the frangible positioning elements 332-1. As depicted, the wing flanges 318 may, in the first position be disposed a first distance "A" into the anti-rotation features 332 (FIG. 3A) and/or be disposed a first distance "B" from the terminus of the anti-rotation features 332 (FIG. 3B). In some embodiments, contact between the frangible positioning elements 332-1 and the wing flanges 318 may define the first position between the BFS vial 310 and the mounting collar 330 (and/or the first stage of the pre-filled dual-chamber medical agent delivery system 300).

Figure 3C:
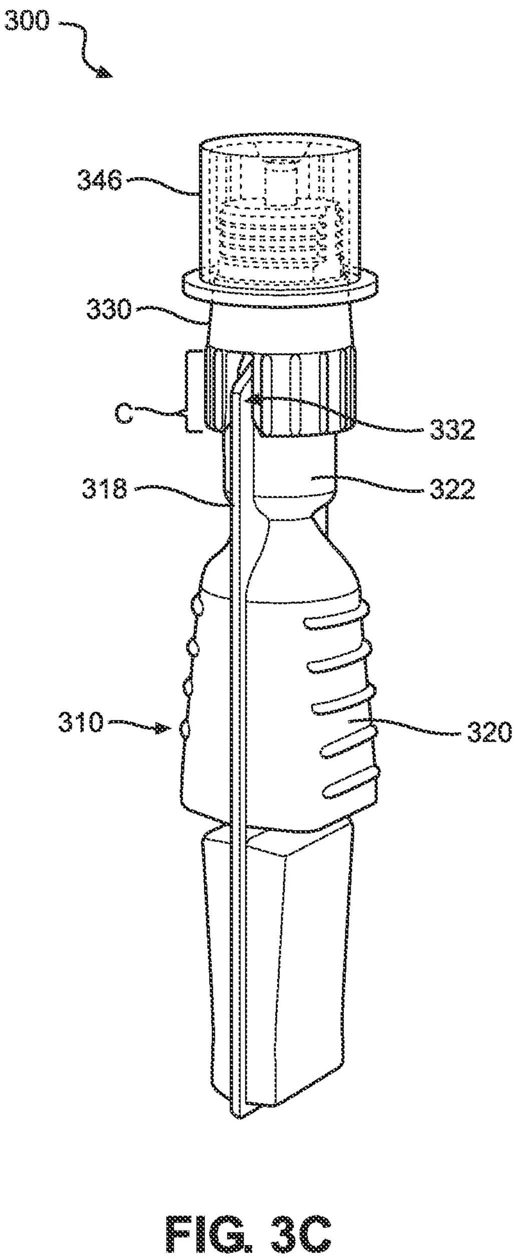
Figure 3D:
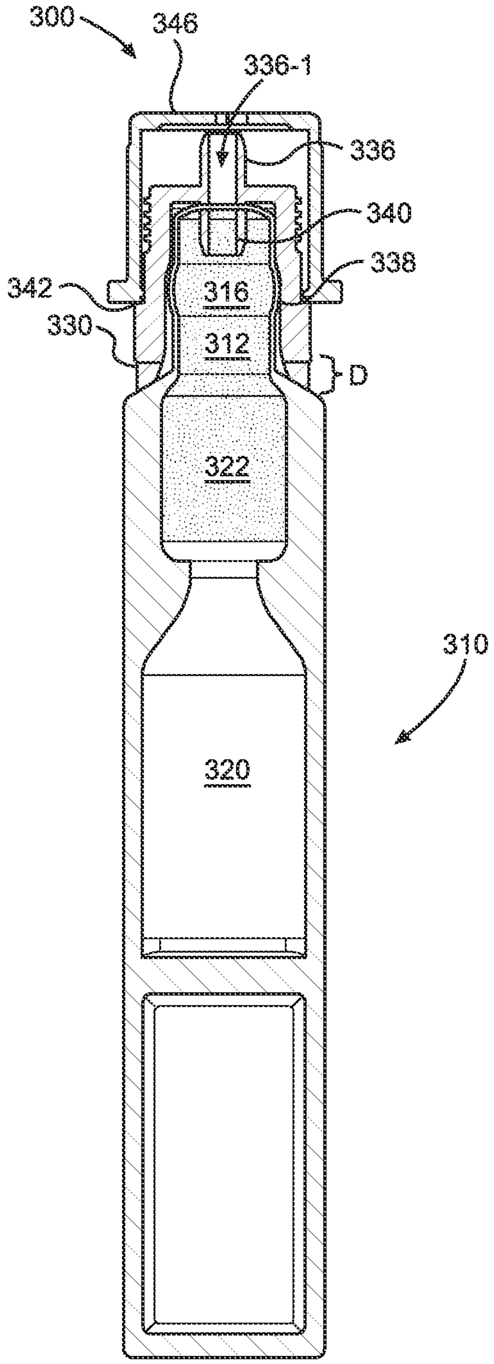

According to some embodiments, in a second stage or position (e.g., corresponding to the second state of the pre-filled dual-chamber medical agent delivery system 300) as depicted in FIG. 3C and FIG. 3D, the BFS vial 310 may be fully inserted into the mounting collar 330 such that the piercing element 340 pierces the fluid seal 314 and/or such that the mounting flange 316 is retained by and/or seated in the mounting recess 338. In some embodiments, a second and/or greater axial force may be applied to further urge the BFS vial 310 into the mounting collar 330 (e.g., causing a transition from the first stage to the second stage) such that the leading edges of the wing flanges 318 sever, fracture, and/or otherwise cause the frangible positioning elements 332-1 to fail. In such embodiments, the wing flanges 318 may then travel deeper into the anti-rotation elements 332 than originally positioned in the first position/stage. As depicted, the wing flanges 318 may, in the second position be disposed a second distance "C" into the anti-rotation features 332 (FIG. 3C) and/or be disposed a second distance "D" from the terminus of the anti-rotation features 332 (FIG. 3D). In some embodiments, the second distance "C" into the anti-rotation features 332 may be greater than the first distance "A" into the anti-rotation features 332 and/or the second distance "D" from the terminus of the anti-rotation features 332 may be less than the first distance "B" from the terminus of the anti-rotation features 332.

In some embodiments, the pre-filled dual-chamber medical agent delivery system 300 may be provided to a user (not shown; e.g., a nurse, doctor, or patient—e.g., in the case of self-injection) in the first state, such that the mounting collar 330 is already partially engaged with and/or coupled to the BFS vial 310 (e.g., the first axial force has already been applied during a manufacturing assembly process). In some embodiments, the mounting collar 330 and the BFS vial 310 may be provided separately, and the user may need to achieve the first state by aligning the mounting collar 330 and the neck 312 of the BFS vial 310 and applying the first axial force. According to some embodiments, once the pre-filled dual-chamber medical agent delivery system 300 is transitioned to the first state, a first step for employing the pre-filled dual-chamber medical agent delivery system 300 may be to apply axial compressive force (e.g., the second axial force) further urging the BFS vial 310 axially into the mounting collar 330, severing the frangible positioning elements 332-1, and seating the mounting flange 316 in the mounting recess 338 (e.g., thereby achieving the second state of the pre-filled dual-chamber medical agent delivery system 300). As depicted by the downward arrow in FIG. 3A and FIG. 3B, the force may be applied to the collar cap 346, which transfers the force advantageously to the mounting collar 330 (e.g., via engagement with the exterior flange 342 and/or via the fluid outlet 336). While not depicted for ease of illustration and description, the BFS vial 310 may be held stationary or may be urged axially toward the mounting collar 330 to effectuate the achievement of the first state and/or the second a state.

Figure 3E:
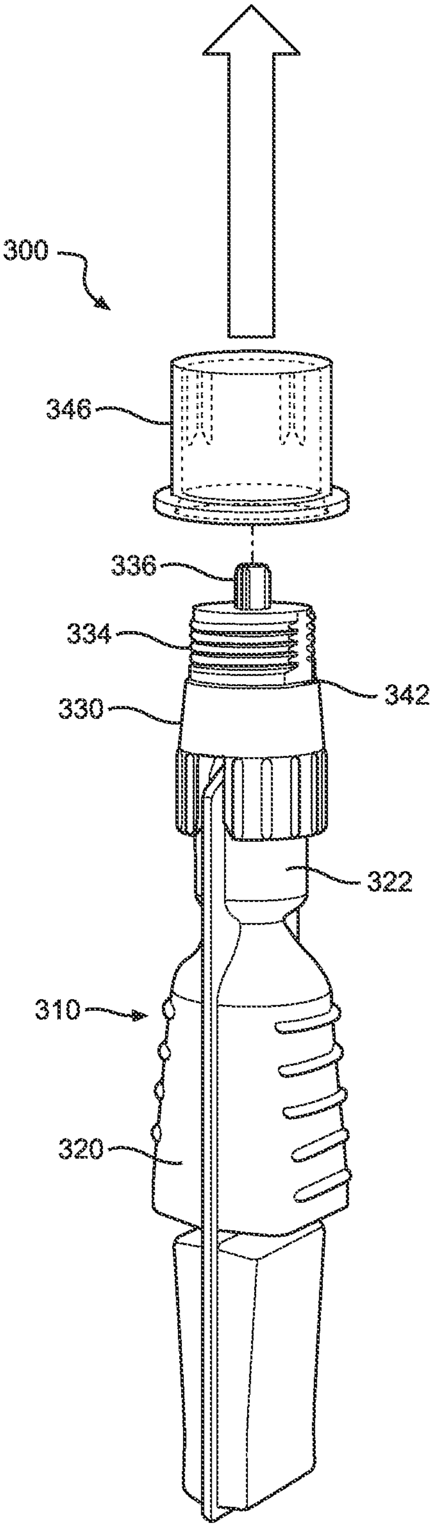
Figure 3F:
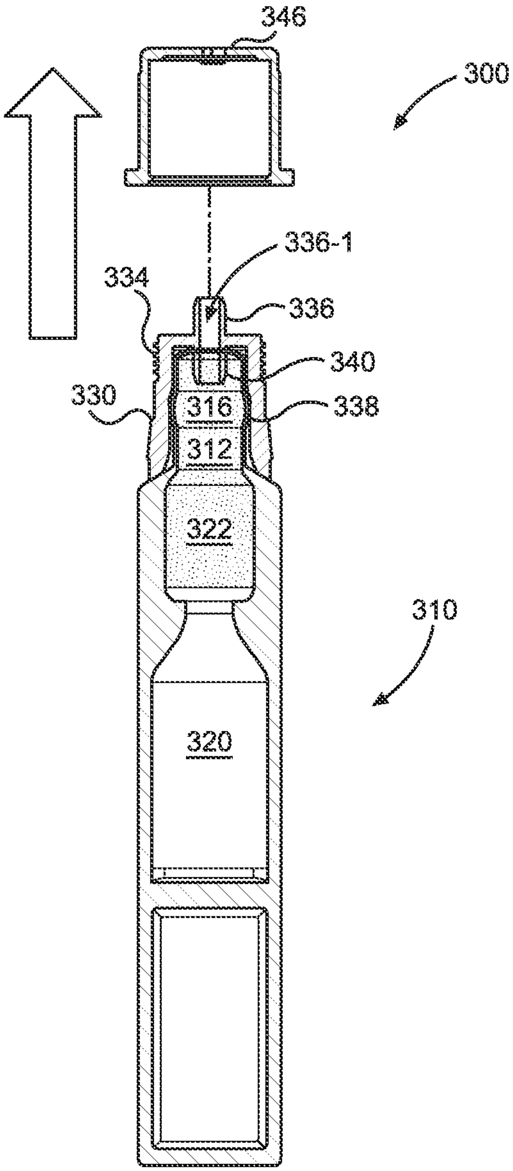

According to some embodiments, a second step for employing the pre-filled dual-chamber medical agent delivery system 300 may comprise transitioning the pre-filled dual-chamber medical agent delivery system 300 to a third state, as depicted in FIG. 3E and FIG. 3F. In the second step, for example, the collar cap 346 may be removed, exposing the fluid outlet 336. In some embodiments, the first reservoir 320 may comprise a first fluid such as air and/or the second reservoir 322 may comprise a second fluid such as a diluent or other liquid or ingredient (together, for example, defining a "first chamber" of the pre-filled dual-chamber medical agent delivery system 300). In the third state with the collar cap 346 removed, a squeezing or other collapsing or compression of the first reservoir 320 may cause the first fluid to exert pressure on the liquid, thereby expelling the liquid through the outlet port 336. In embodiments where it is desired to inject or otherwise selectively administer or utilize the liquid, care would be taken not to squeeze the first reservoir 320 until further states of the pre-filled dual-chamber medical agent delivery system 300 are achieved. In some embodiments, in the third state, the combined BFS vial 310 and mounting collar 330 (e.g., a "first piece" of the pre-filled dual-chamber medical agent delivery system 300; e.g., a BFS module and/or assembly) may be considered "activated" (e.g., ready to dispense the liquid/agent).

Figure 3G:
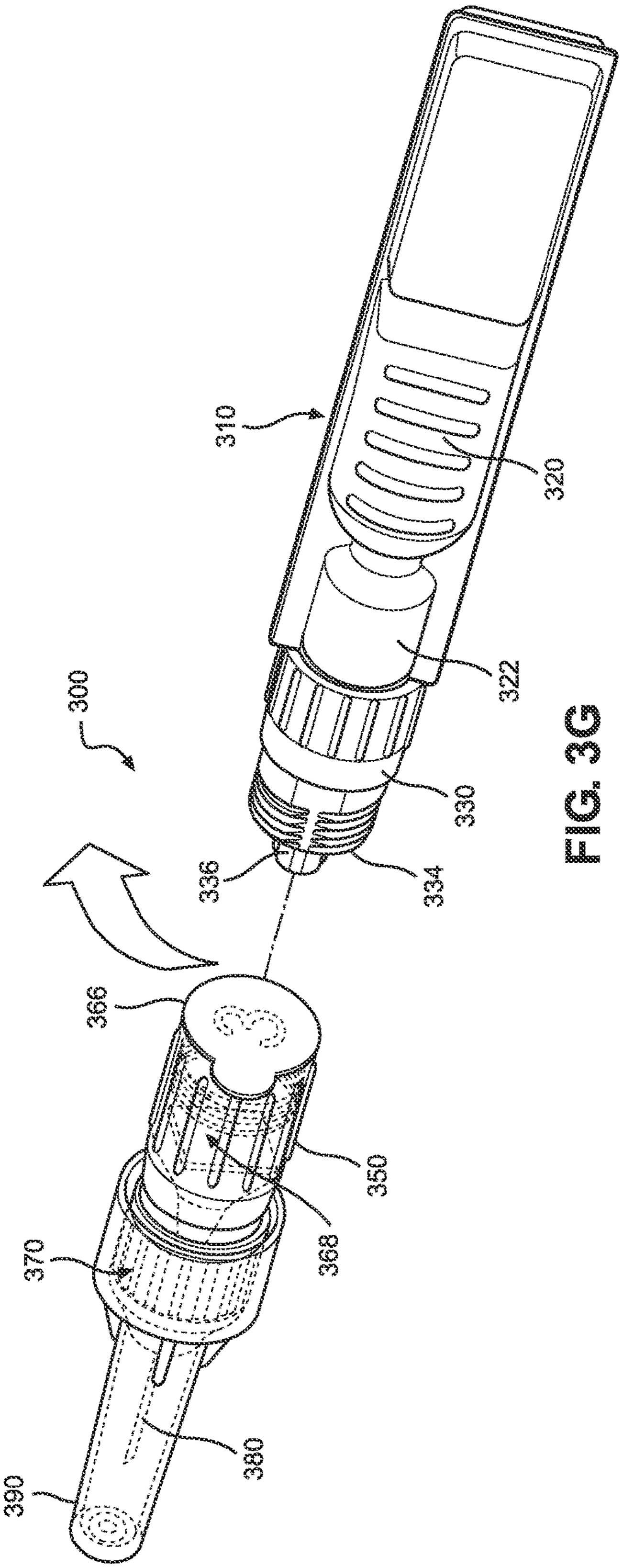
Figure 3H:
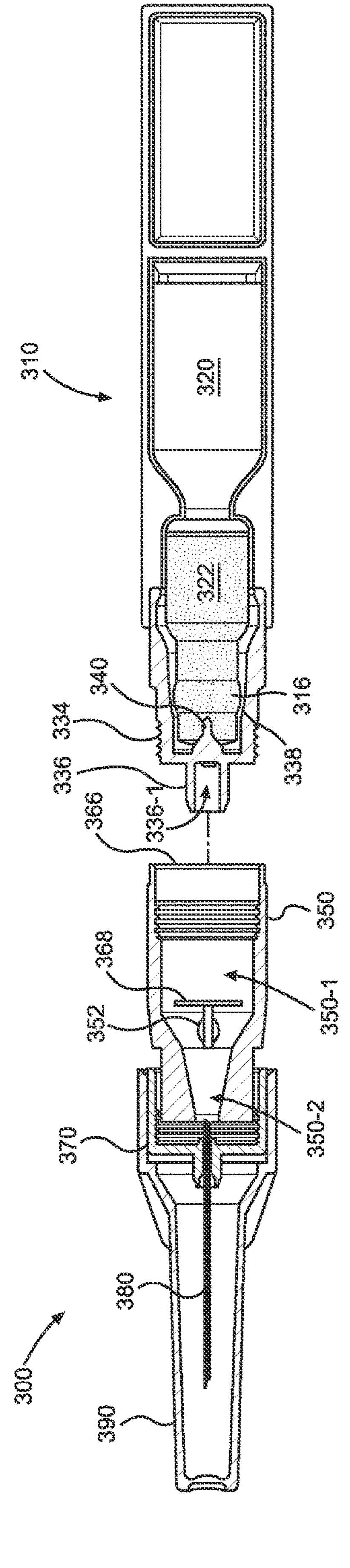

According to some embodiments, and referring to FIG. 3G, FIG. 3H, FIG. 3I, FIG. 3J, and FIG. 3N, the pre-filled dual-chamber medical agent delivery system 300 may comprise a "second piece" comprising (i) a dry ingredient chamber 350 (e.g., a "second chamber") defining an interior inlet volume 350-1 and/or an interior outlet volume 350-2, one or more dry ingredient retention features 352, internal threads 354 disposed at a first end, an end seal 356 disposed at a second end (specifically depicted FIG. 3N), and/or external threads 358 disposed at or proximate to the second end thereof (also specifically depicted FIG. 3N), (ii) a seal 366 covering the first end of the dry ingredient chamber 350 (specifically depicted FIG. 3G), (iii) a dry ingredient 368 disposed within the interior inlet volume 350-1, (iv) a needle hub 370 comprising internal threads 372 and defining a needle bore 374 (each specifically depicted FIG. 3N), (v) a needle 380 coupled through the needle hub bore 374 and defining a first piercing end 382 (also specifically depicted FIG. 3N) and a second piercing end 384, and/or (vi) a needle cap 390 coupled to cover the needle 380 (or at least the second piercing end 384 thereof). As depicted in FIG. 3G and FIG. 3H, the "second piece" may be provided pre-assembled with the external threads 358 of the dry ingredient chamber 350 being at least partially engaged with the cooperative internal threads 372 of the needle hub 370. In such a manner, for example, the needle cap 390 and the seal 366 may prevent contaminants from being introduced into the dry ingredient chamber 350 and/or the needle 380.

Figure 3I:
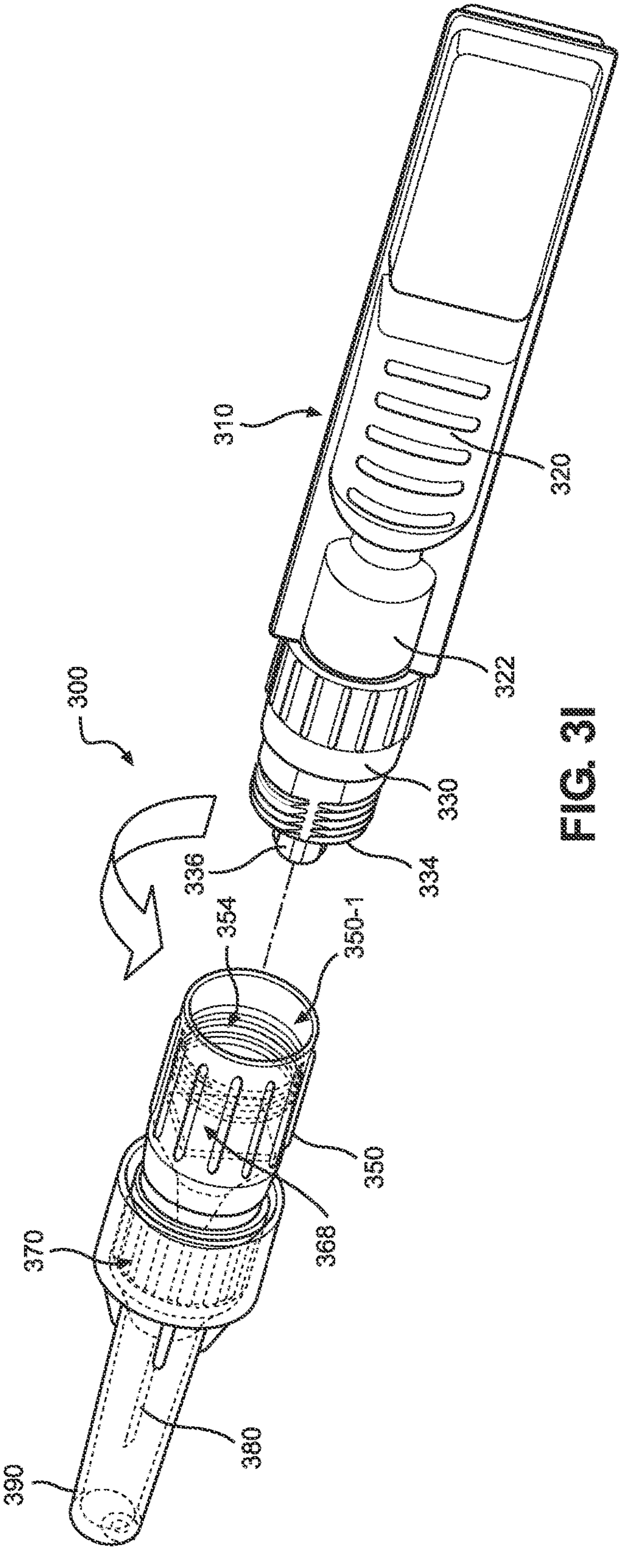
Figure 3J:
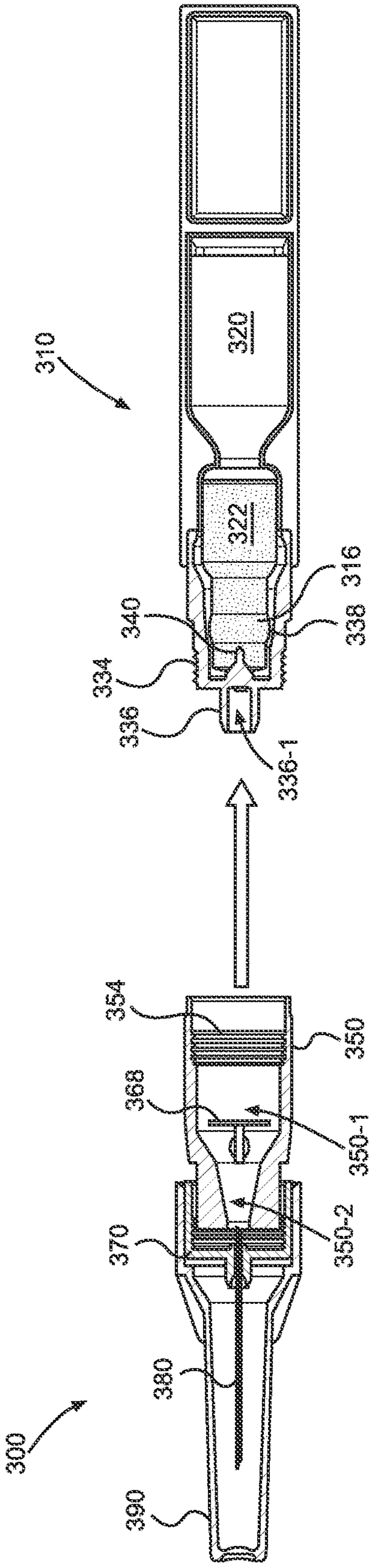
Figure 3K:
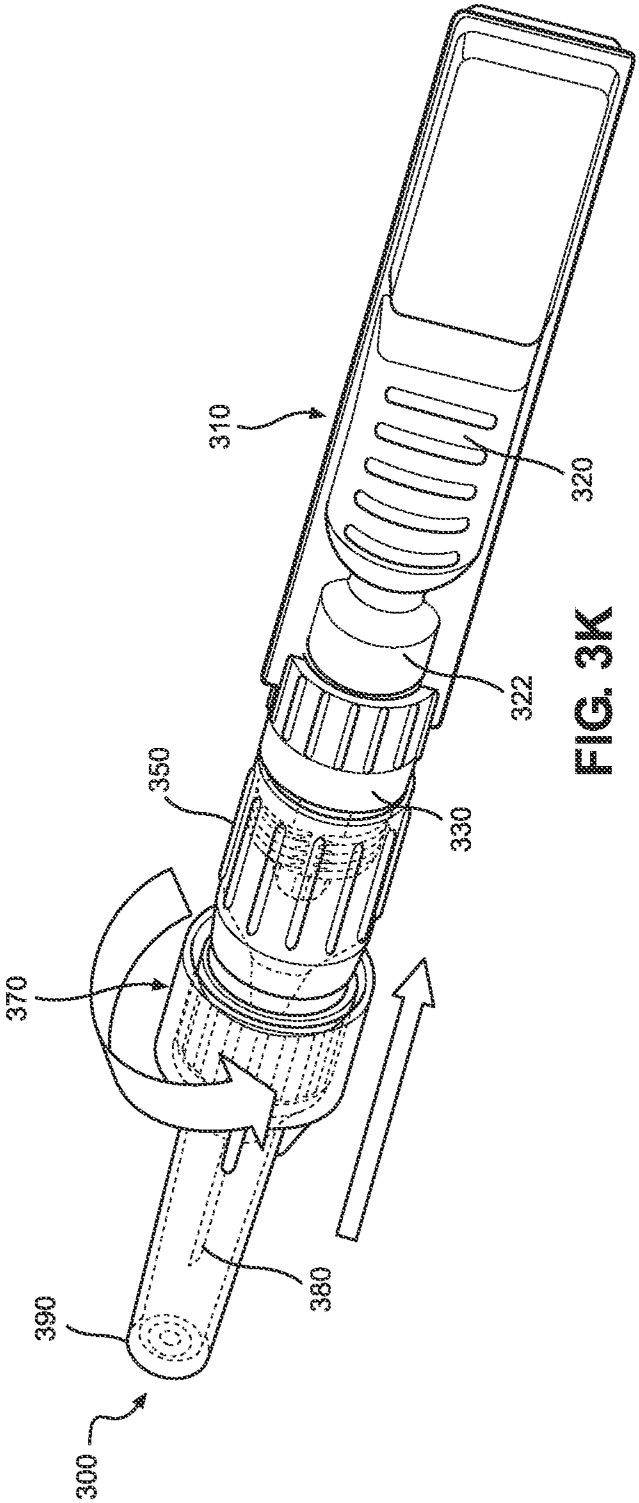
Figure 3L:
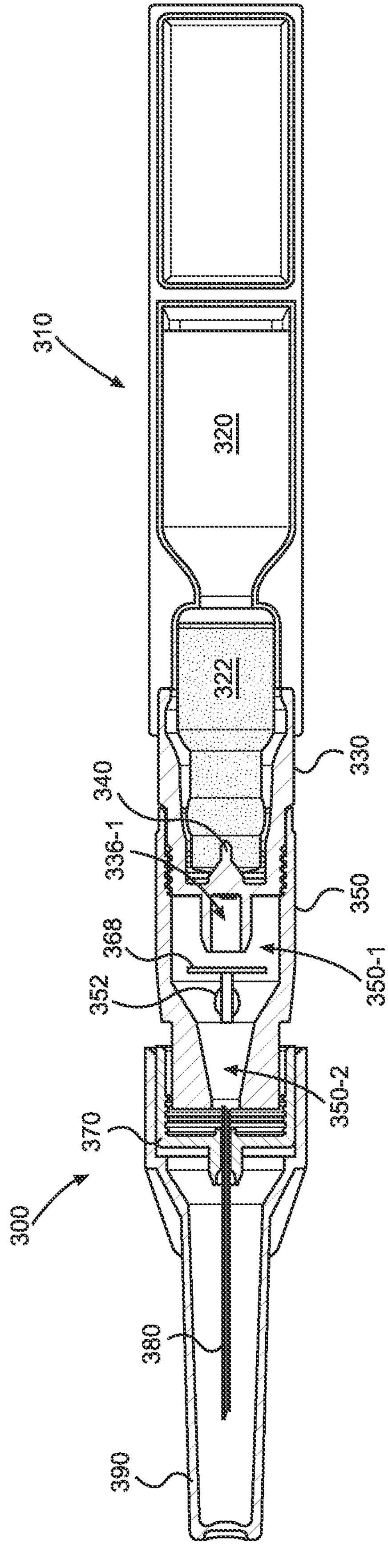

In some embodiments, a third step for employing the pre-filled dual-chamber medical agent delivery system 300 may comprise transitioning the pre-filled dual-chamber medical agent delivery system 300 to a fourth state, as depicted in FIG. 3G and FIG. 3H. In the third step, for example, the seal 366 may be removed, exposing the interior inlet volume 350-1 of the dry ingredient chamber 350. In some embodiments, the seal 366 may comprise a foil, paper, wax, and/or other seal affixed and/or printed with an indication of the corresponding sequence or step number, e.g., "3" as depicted in FIG. 3G. According to some embodiments, a fourth step for employing the pre-filled dual-chamber medical agent delivery system 300 may comprise transitioning the pre-filled dual-chamber medical agent delivery system 300 to a fifth state, as depicted in FIG. 3I and FIG. 3J. In the fourth step, for example, the exposed external threads 334, outlet port 336, and/or second end of the mounting collar 330 may be inserted into the interior inlet volume 350-1 of the dry ingredient chamber 350 and the "first piece" and the "second piece" may be rotated (or otherwise coupled) together to engage and advance the corresponding external threads 334 of the mounting collar 330 with the internal threads 354 of the dry ingredient chamber 350. Counter-directional rotational forces may be applied to each of the dry ingredient chamber 350 and the mounting collar 350, for example, to achieve a secure coupling therebetween. In some embodiments, once the "first piece" and the "second piece" and/or the dry ingredient chamber 350 and the mounting collar 330 are coupled together, the fluid outlet 336 (and accordingly the first reservoir 320 and the second reservoir 322) of the mounting collar 330 may be placed in fluid communication with the interior inlet volume 350-1 (and accordingly the interior outlet volume 350-2 and the dry ingredient 368) of the dry ingredient chamber 350.

According to some embodiments, a fifth step for employing the pre-filled dual-chamber medical agent delivery system 300 may comprise transitioning the pre-filled dual-chamber medical agent delivery system 300 to a sixth state, as depicted in FIG. 3K, FIG. 3L, FIG. 3M, and FIG. 3N. In the fifth step, for example, the needle hub 370 may be completely engaged with and/or coupled to the dry ingredient chamber 350. The external threads 358 of the dry ingredient chamber 350 may be transitioned from being only partially engaged with the cooperative internal threads 372 of the needle hub 370, for example, by application of counter-directional rotational forces applied to each of the dry ingredient chamber 350 and the needle hub 370 to achieve a secure coupling therebetween. According to some embodiments, such as in the case that the needle cap 390 covers the needle hub 370, rotational force may be applied to the needle cap 390. The needle cap 390 may be configured (e.g., with one or more internal keys or features; not separately shown or labeled), for example, to transfer received rotational force (at least in one direction) to the needle hub 370. In some embodiments, advancement of the cooperative internal threads 372 and external threads 358 may cause the first piercing end 382 of the needle 380 to advance axially toward the end seal 356. The sixth state may be achieved, in some embodiments, in the case that the advancement/coupling causes the first piercing end 382 of the needle 380 to advance through the end seal 356 (as shown in FIG. 3M and FIG. 3N), thereby placing the needle 380 in fluid communication with the interior outlet volume 350-2 (and accordingly, with any other feature in fluid communication therewith—e.g., the BFS vial 310). According to some embodiments, in the sixth state, the pre-filled dual-chamber medical agent delivery system 300 (e.g., the coupled "first piece" and "second piece" of the pre-filled dual-chamber medical agent delivery system 300) may be considered "activated" (e.g., ready to dispense the combined agent).

Figure 3O:
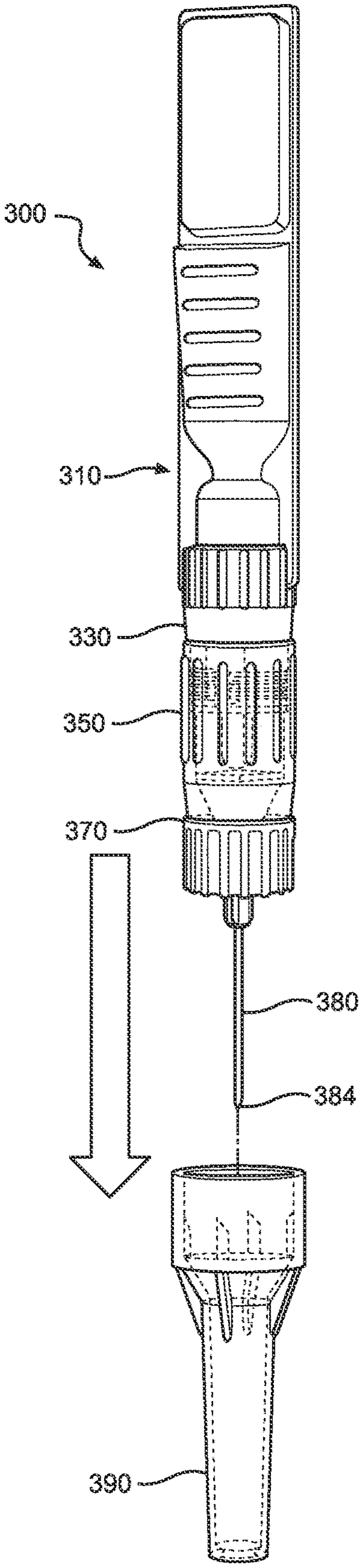
Figure 3P:
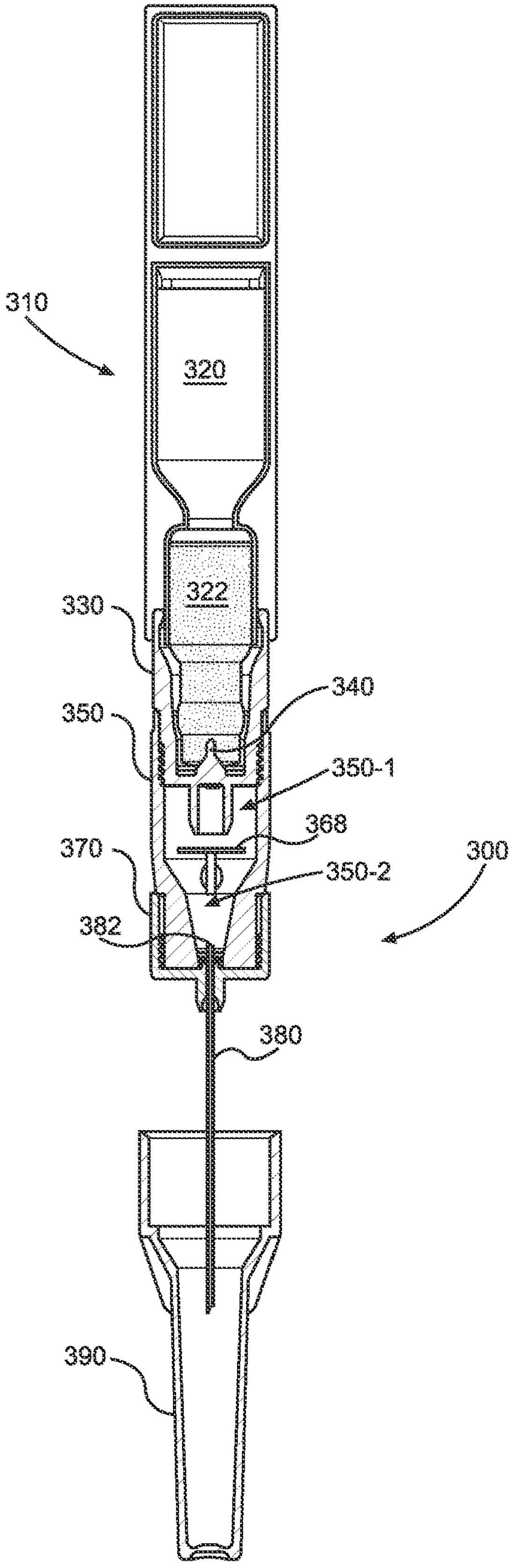
Figure 3Q:
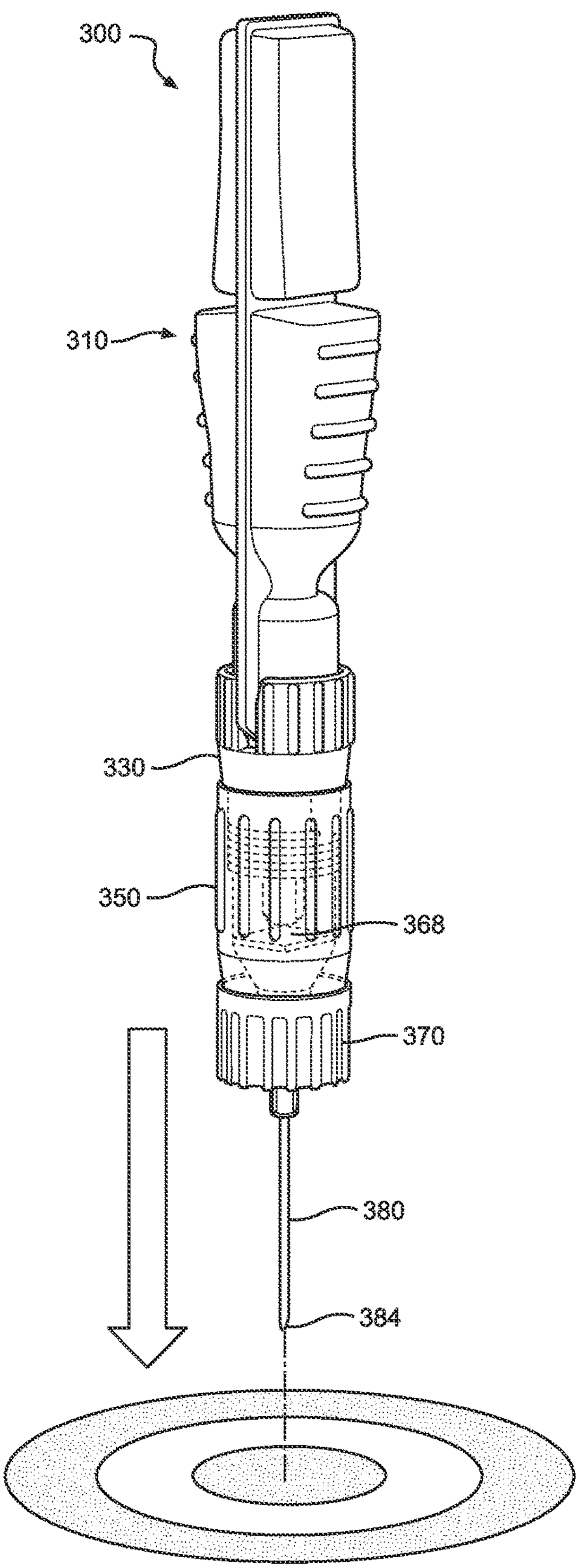
Figure 3R:
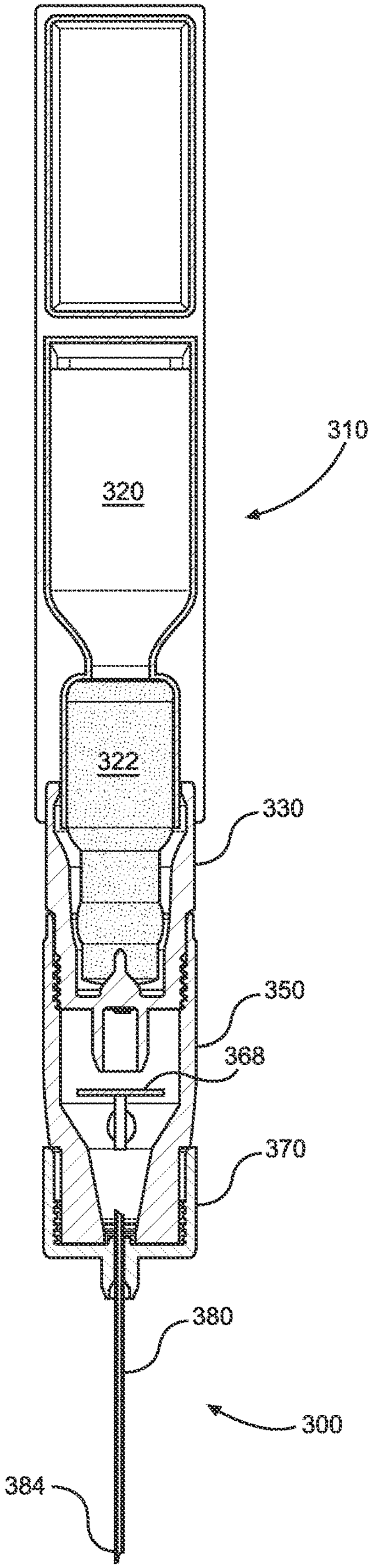

In some embodiments, a sixth step for employing the pre-filled dual-chamber medical agent delivery system 300 may comprise transitioning the pre-filled dual-chamber medical agent delivery system 300 to a seventh state, as depicted in FIG. 3O and FIG. 3P. In the sixth step, for example the needle cap 390 may be removed (e.g., via application of an axial separation force) and discarded (or set aside for later reinstallation to minimize hazards). Removal of the needle cap 390 may, for example, expose the second piercing end 384 (e.g., an administration end) of the needle 380. According to some embodiments, a seventh step for employing the pre-filled dual-chamber medical agent delivery system 300 may comprise transitioning the pre-filled dual-chamber medical agent delivery system 300 to an eighth state, as depicted in FIG. 3Q and FIG. 3R. In the seventh step, for example the activated pre-filled dual-chamber medical agent delivery system 300 may be positioned for injection into a desired target.

Figure 3S:
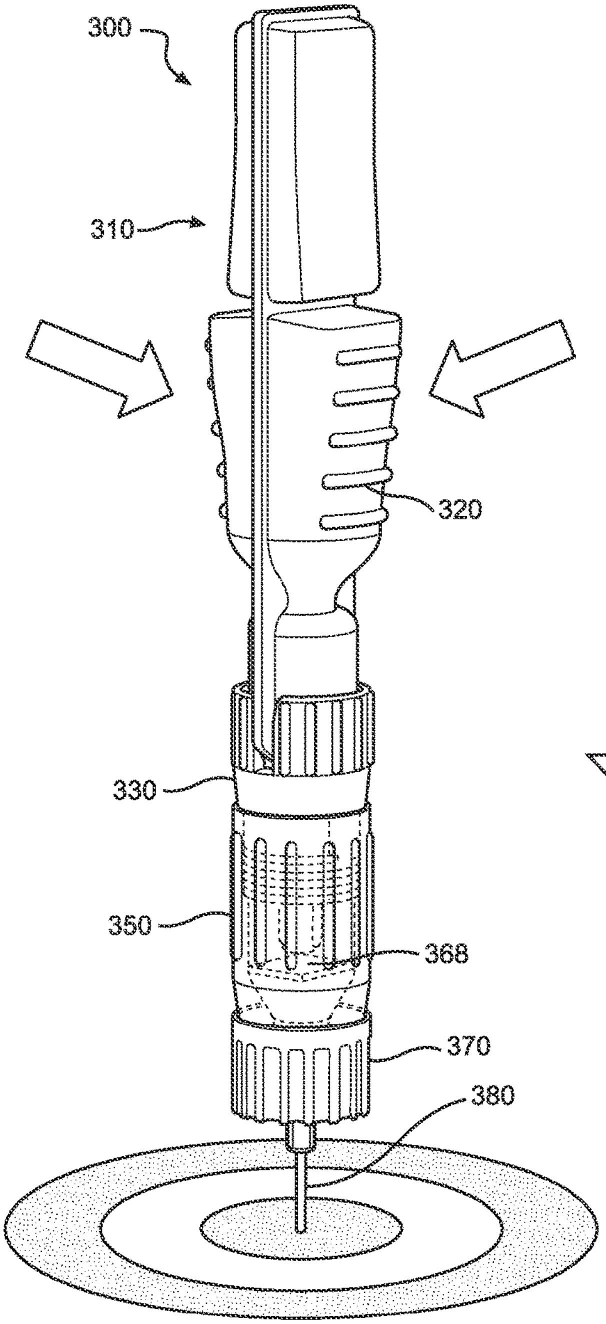
Figure 3T:
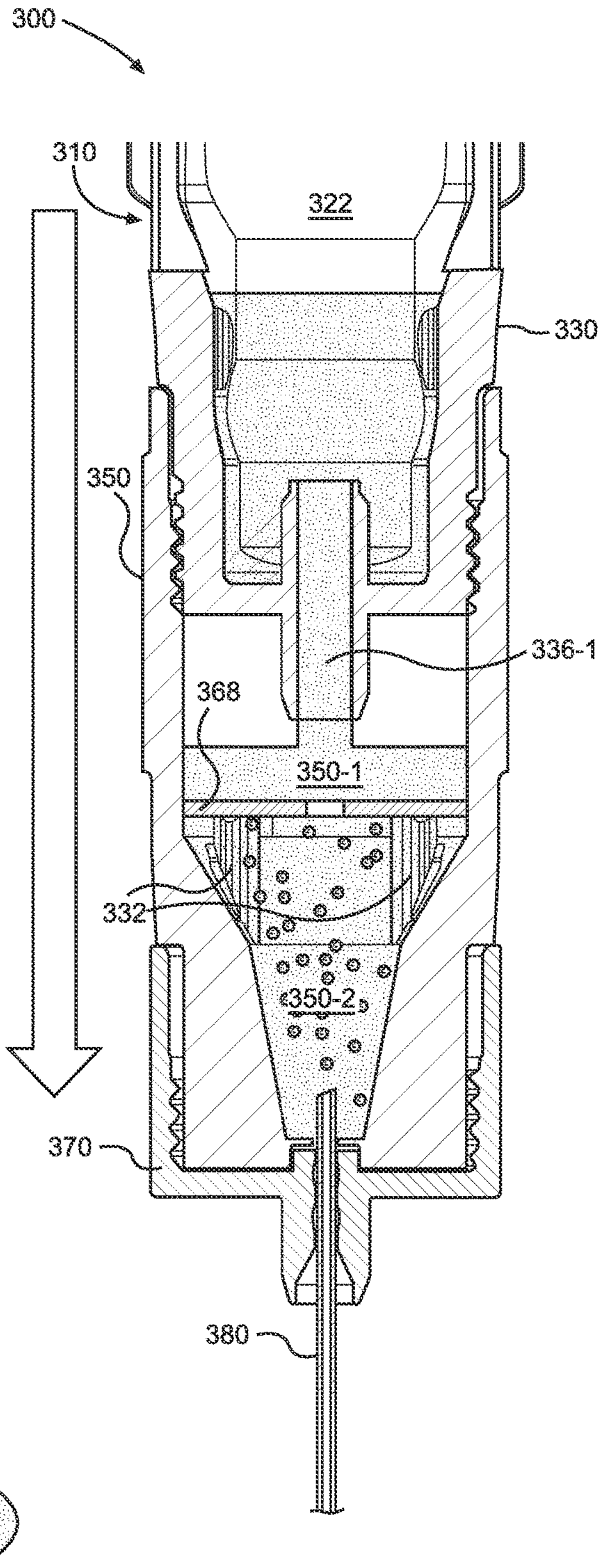

According to some embodiments, an eighth step for employing the pre-filled dual-chamber medical agent delivery system 300 may comprise transitioning the pre-filled dual-chamber medical agent delivery system 300 to a ninth state, as depicted in FIG. 3S and FIG. 3T. In the eighth step, for example, the pre-filled dual-chamber medical agent delivery system 300 may be engaged to administer the combined fluid agent/medicament to the patient. The second piercing end 384 of the needle 380 (and/or other administration member) may be inserted into (or otherwise engaged with) the target, for example, and the first reservoir 320 may be compressed (via application of an radially inward force (s); e.g., a squeezing). In some embodiments, compression of the first reservoir 320 may force any fluid (e.g., air) components therein to expel the liquid from the second reservoir 322, through the fluid outlet conduit 336-1, and into the interior inlet volume 350-1 where it contacts and/or interacts with the dry ingredient 368. As depicted in FIG. 3S for example, the liquid may be forced through and/or past the dry ingredient 368 such that a combination of the liquid and the dry ingredient 368 is mixed in the interior outlet volume 350-2 (or "mixing chamber"). The combined agent may further, for example, by expelled through the needle 380 and into the target.

Figure 3U:
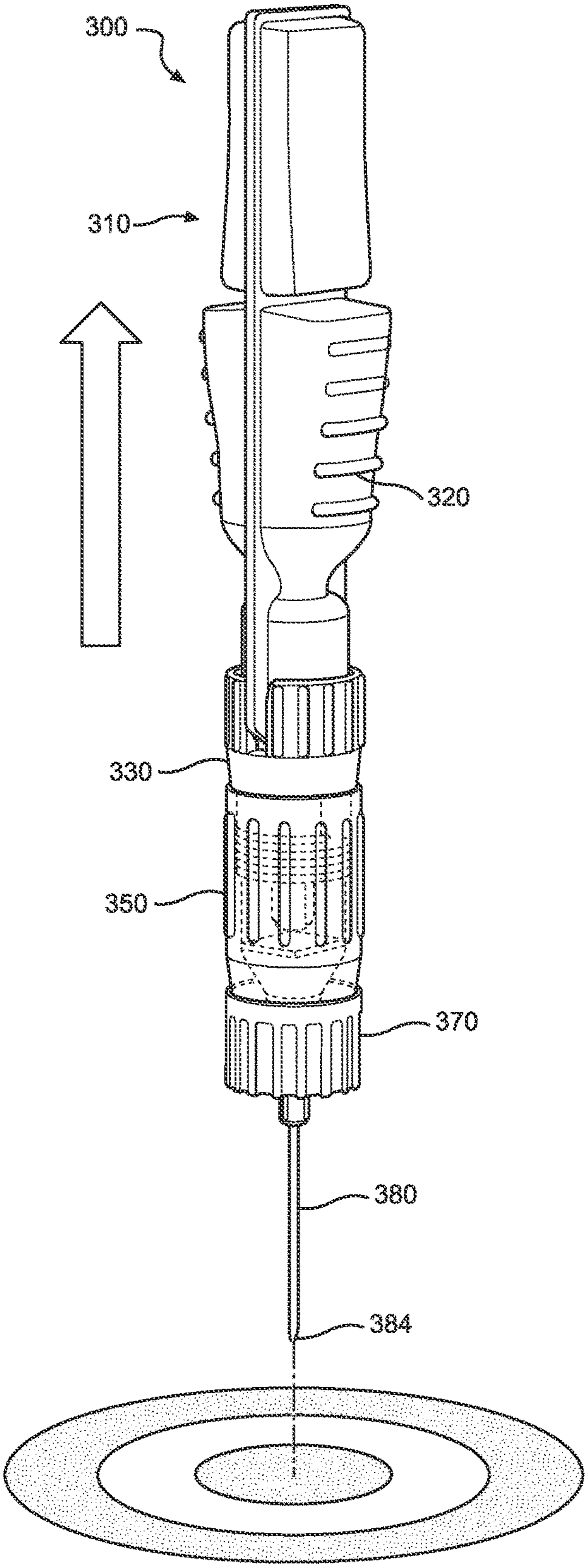
Figure 3V:
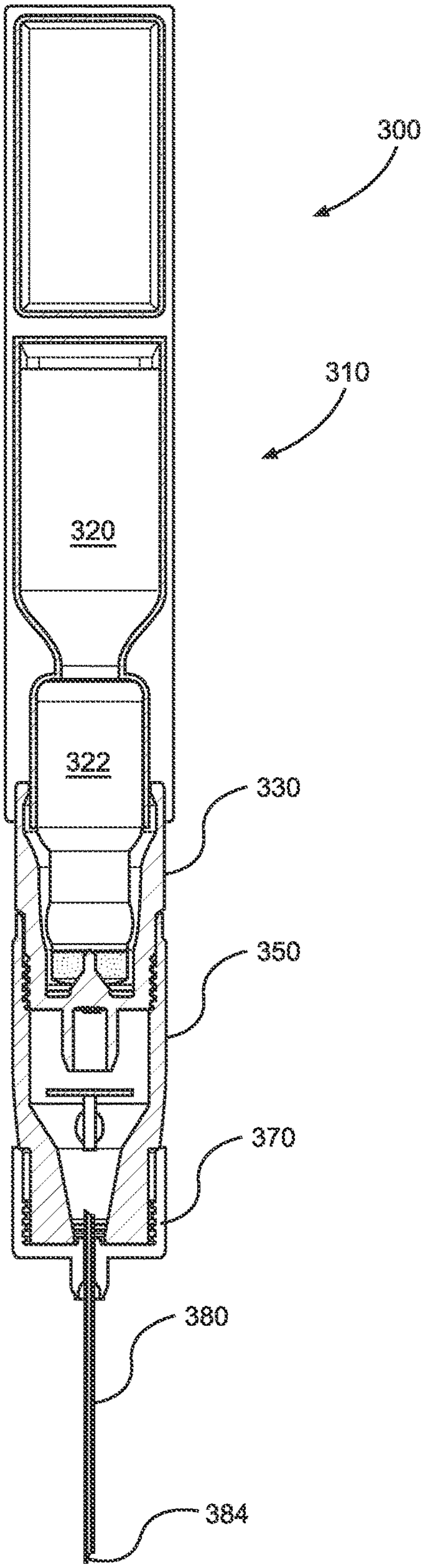
Figure 4A:
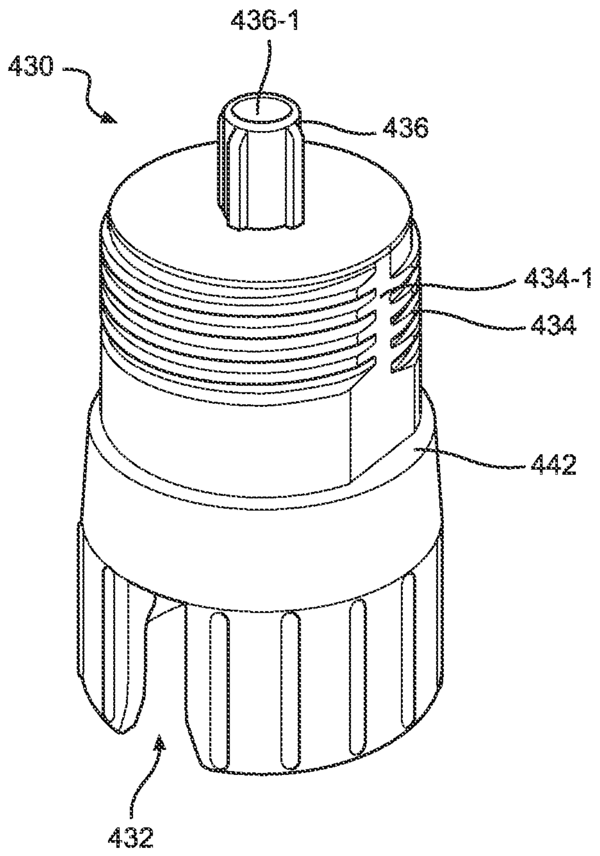
FIG. 4A, FIG. 4B, FIG. 4C, FIG. 4D, FIG. 4E, and FIG. 4F are perspective, left, right, top, bottom, and side cross-section views of a BFS connector according to some embodiments.
Figure 4B:
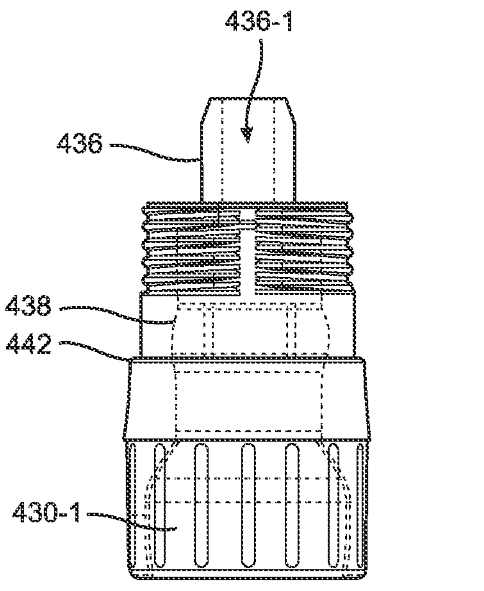
Figure 4C:
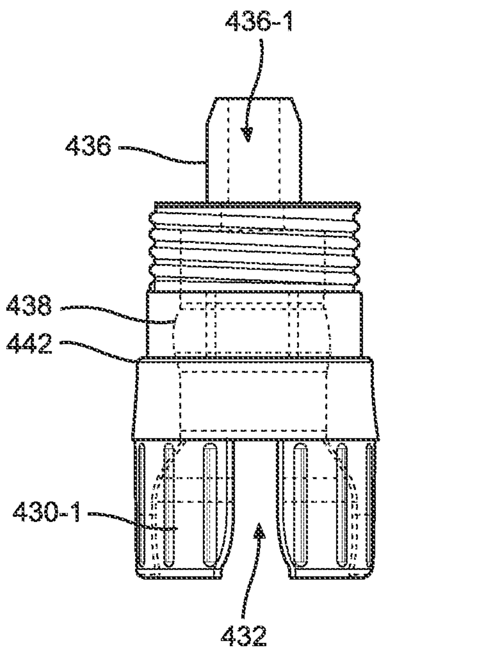
Figure 4D:
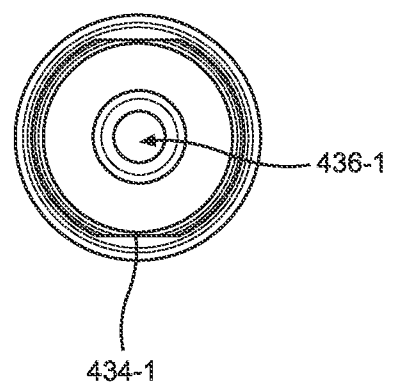
Figure 4E:
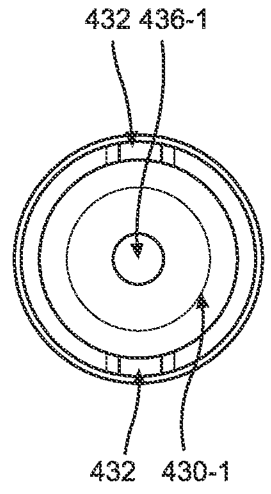
Figure 4F:
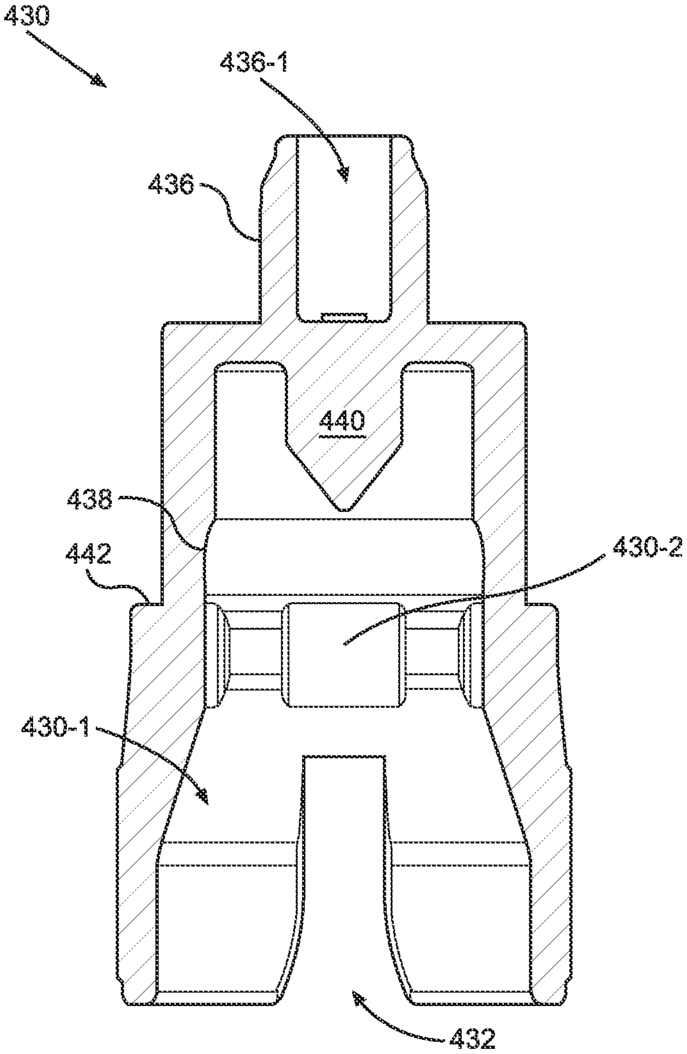

In some embodiments, a nineth step for employing the pre-filled dual-chamber medical agent delivery system 300 may comprise transitioning the pre-filled dual-chamber medical agent delivery system 300 to a tenth state, as depicted in FIG. 3U and FIG. 3V. In the nineth step, for example the needle 380 may be removed from the patient/target, such as by backing the needle 380 out of the target site. According to some embodiments, it may be desirable to maintain pressure upon the first reservoir 320 to maintain the first reservoir 320 in a compressed state until the needle 380 has been removed from the target, such as to prevent application of suction forces to the target. Upon removal of the needle 380, the pressure may be removed and the first reservoir 320 may once again return to an uncompressed configuration (e.g., the first reservoir 320 may be elastic), rendering the pre-filled dual-chamber medical agent delivery system 300 empty, inert, and/or ready for disposal.

In some embodiments, fewer or more components 310, 312, 314, 316, 318, 320, 322, 330, 332, 332-1, 334, 336, 336-1, 338, 340, 350, 350-1, 350-2, 352, 354, 356, 358, 366, 368, 370, 372, 374, 380, 382, 384, 390 and/or various configurations of the depicted components 310, 312, 314, 316, 318, 320, 322, 330, 332, 332-1, 334, 336, 336-1, 338, 340, 350, 350-1, 350-2, 352, 354, 356, 358, 366, 368, 370, 372, 374, 380, 382, 384, 390 may be included in the pre-filled dual-chamber medical agent delivery system 300 without deviating from the scope of embodiments described herein. In some embodiments, the components 310, 312, 314, 316, 318, 320, 322, 330, 332, 332-1, 334, 336, 336-1, 338, 340, 350, 350-1, 350-2, 352, 354, 356, 358, 366, 368, 370, 372, 374, 380, 382, 384, 390 may be similar in configuration and/or functionality to similarly named and/or numbered components as described herein. In some embodiments, the pre-filled dual-chamber medical agent delivery system 300 (and/or portions thereof) may comprise a disposable, single-dose delivery assembly operable to be utilized to execute, conduct, and/or facilitate the method 600 of FIG. 6 herein, and/or portions thereof.

Referring additionally to FIG. 4A, FIG. 4B, FIG. 4C, FIG. 4D, FIG. 4E, and FIG. 4F, perspective, left, right, top, bottom, and side cross-section views of a BFS coupling 430 according to some embodiments are shown. The BFS coupling 430 may comprise similar features and/or configurations and/or may be similar to the connector 130, adapter 230, and/or mounting collar 330 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein. The BFS coupling 430 may comprise, for example, a generally cylindrical body defining an interior volume 430-1. In some embodiments, a pathway into the interior volume 430-1 may be modified from a simply circular (or other chosen geometry) cross-section to provide for easier entry of an inserted mounting flange of a BFS vial (not shown). As depicted for example, the interior volume 430-1 may comprise a one or more radially spaced undercuts 430-2 that locally increase the interior diameter of the interior volume 430-1 to provide less friction to a mounting flange urged axially into the interior volume 430-1.

According to some embodiments, the BFS coupling 430 may comprise one or more anti-rotation coupling features 432 (e.g., axial slits, as depicted) disposed at a first end and/or external threads 434 disposed at a second end thereof. According to some embodiments, the BFS coupling 430 may comprise one or more thread interruptions 434-1 that provide for areas of increased wall thickness to reduce the likelihood of structural failure in the case that the threads 434 receive a rotational force (e.g., torque) when mated with a corresponding object (not shown; e.g., the modular chamber element 150, mixing chamber 250, and/or dry ingredient chamber 350 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG.

3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein).

In some embodiments, the BFS coupling 430 may comprise or define a neck, stem, or nozzle 436 defining an interior bore or outlet channel 436-1 that is in fluid communication with the interior volume 430-1. According to some embodiments, the BFS coupling 430 may comprise an internal groove or seat 438 that is cooperatively sized and configured to receive a mounting flange of a BFS vial (neither shown; e.g., the mounting flange/feature 116, 216, 316 of the BFS vials 110, 310 and/or the plastic bottle 210 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein). In some embodiments, the BFS coupling 430 may comprise and/or define a piercing element 440. The piercing element 440 may comprise an angled and/or sharpened protrusion of "hard" plastic, for example, that is disposed within the interior volume 430-1 such that in the case that a BFS vial is seated in the interior volume 430-1 and/or a mounting flange thereof is seated in the seat 438, the piercing element 440 may engage with and puncture a seal of the BFS vial (not shown; e.g., the fluid seal 114, 214, 314 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein). According to some embodiments, the outlet channel 436-1 may extend through and/or be at least partially defined by the piercing element 440 such that fluid released from the BFS vial due to a piercing of the seal by the piercing element 440 may be administered through (e.g., selectively) the outlet channel 436-1. According to some embodiments, the piercing element 440 may also or alternatively comprise a pointed or sharpened metal tube coupled to the BFS coupling 430 and/or disposed in and/or forming the outlet channel 436-1.

In some embodiments, the body of the BFS coupling 430 may be sized to permit a user to have a suitable gripping surface (e.g., a "hard" plastic gripping surface) such that the BFS coupling 430 may be utilized to attached/engage various components such as an administration member (not shown) with the BFS vial and/or "soft" plastic neck thereof (e.g., without requiring such gripping forces to be applied directly to the BFS vial, which would cause deformation thereof). The length of the body of the BFS coupling 430 may, for example, be sized between twelve millimeters (12 mm) and twenty millimeters (20 mm). According to some embodiments, the one or more anti-rotation coupling features 432 may comprise one or more axial slits. In some embodiments, the one or more anti-rotation coupling features 432 may comprise a plurality of indents, seats, or grooves such as a "castle" nut configuration (not shown). In the case of the slit configuration of the one or more anti-rotation coupling features 432, such features 432 may engage with and/or house or retain (e.g., prevent rotation of) a bottle flange of the BFS vial (not shown; e.g., the bottle flange 118 the side flange 218, and/or the wing flange 318 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein). In the case of the castle nut configuration of the one or more anti-rotation coupling features 432, such features 432 may engage with and/or house or retain (e.g., prevent rotation of) a portion of a bottle flange of the BFS vial that extends into and/or seats in the interior volume 430-1.

According to some embodiments, the BFS coupling 430 may comprise or define an external flange 442. The external flange 442 may, for example, permit one or more objects to be coupled to the outlet (e.g., upper, as shown) end of the BFS coupling 430 but to be restrained from traveling onto the BFS coupling 430 beyond the protrusion of the external flange 442. In some embodiments, the external flange 442 may act as a seat for a portion of a cap, modular chamber element, and/or housing (not shown, but as described herein).

In some embodiments, fewer or more components 430-1, 430-2, 432, 434, 434-1, 436, 436-1, 438, 440, 442 and/or various configurations of the depicted components 430-1, 430-2, 432, 434, 434-1, 436, 436-1, 438, 440, 442 may be included in the BFS coupling 430 without deviating from the scope of embodiments described herein. In some embodiments, the components 430-1, 430-2, 432, 434, 434-1, 436, 436-1, 438, 440, 442 may be similar in configuration and/or functionality to similarly named and/or numbered components as described herein. In some embodiments, the BFS coupling 430 may comprise a portion of a pre-filled dual-chamber medical agent delivery system such as a disposable, single-dose delivery assembly operable to be utilized to execute, conduct, and/or facilitate the method 600 of FIG. 6 herein, and/or portions thereof.

Figure 5A:
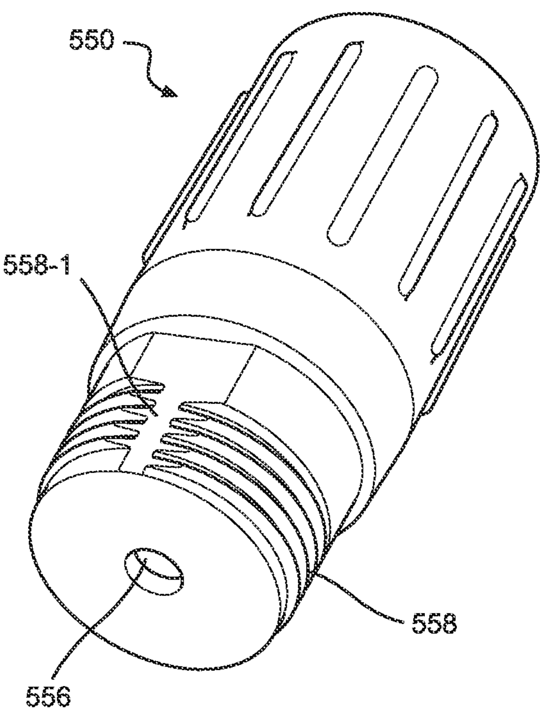
FIG. 5A, FIG. 5B, FIG. 5C, FIG. 5D, FIG. 5E, and FIG. 5F are perspective, left, right, top, bottom, and side cross-section views of a mixing chamber according to some embodiments.
Figure 5B:
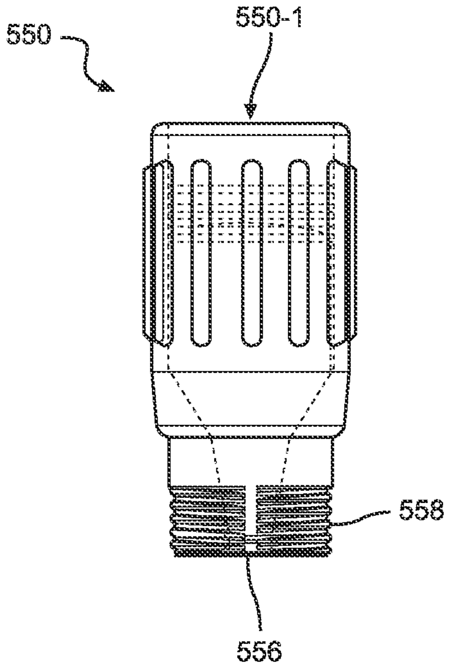
Figure 5C:
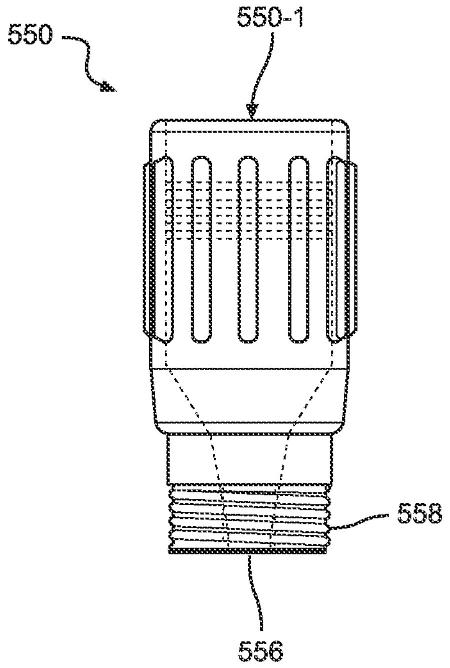
Figure 5D:
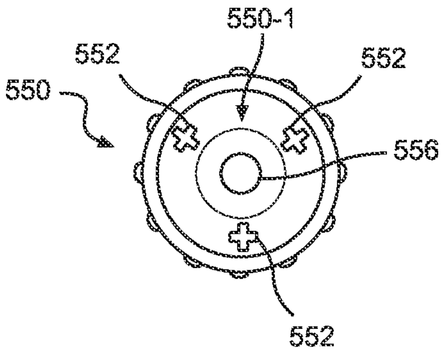
Figure 5E:
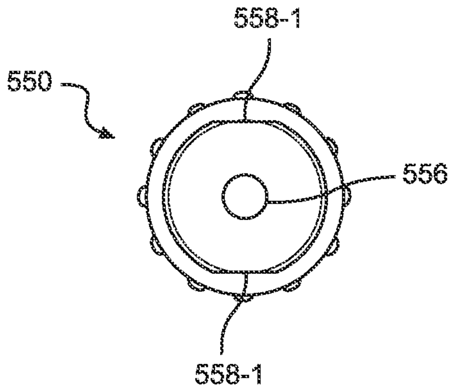
Figure 5F:
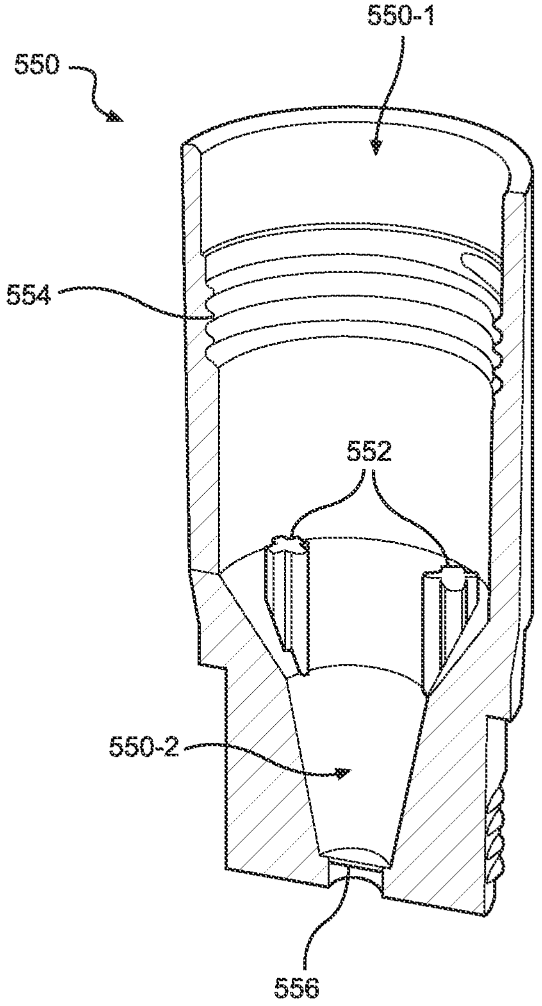

Turning now to FIG. 5A, FIG. 5B, FIG. 5C, FIG. 5D, FIG. 5E, and FIG. 5F, perspective, left, right, top, bottom, and side cross-section views of a mixing chamber 550 according to some embodiments are shown. The mixing chamber 550 may comprise, for example, a generally cylindrically shaped body defining an interior volume 550-1. In some embodiments, the interior volume 550-1 may comprise and/or the mixing chamber 550 may define a nozzle volume 550-2. As depicted in FIG. 5F, the nozzle volume 550-2 may, in some embodiments, be in communication with the interior volume 550-1. According to some embodiments, the interior volume 550-1 and/or the nozzle volume 550-2 may comprise one or more supports or standoffs 552 that are oriented to support and/or attached to a substrate (not shown) that, e.g., may comprise a printed, dried, deposited, lyophilized, and/or other dry form of an active ingredient. In some embodiments, the standoffs 552 may comprise tabs, hooks, shelves, platforms, spikes, grooves, adhesives, hook and/or loop fastener, and/or other features that facilitate the seating and/or retaining of a dry ingredient and/or substrate holding the dry ingredient. In some embodiments, the mixing chamber 550 may comprise internal threads 554 formed on an inside surface of the interior volume 550-1, e.g., at or proximate to a first end of the mixing chamber 550. In some embodiments, the internal threads 554 may be configured to cooperatively and selectively mate with corresponding threads of another object (not shown; e.g., the connector 130, adapter 230, and/or mounting collar 330 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein).

According to some embodiments, the mixing chamber 550 may comprise a seal 556 at or on a second end of the mixing chamber 550, e.g., at a narrowed end of the nozzle volume 550-2. In some embodiments, the seal 556 may comprise a specifically designed thin-walled portion of the mixing chamber 550 such as a bore or hole with only two-tenths millimeters (0.2-mm) thickness. Such a thin portion or membrane may, for example, permit the interior volume 550-1 to remain separated from outside fluids, while also permitting easy selective puncturing thereof, e.g., in the case a user advances a needle or other piercing element to activate a single-dose delivery system (of which the mixing chamber 550 is a part or component) as described herein. In some embodiments, the mixing chamber 550 may comprise external threads 558 at or adjacent to the second end. According to some embodiments, the mixing chamber 550 may comprise one or more thread interruptions 558-1 that provide for areas of increased wall thickness to reduce the likelihood of structural failure in the case that the external threads 558 receive a rotational force (e.g., torque) when mated with a corresponding object (not shown; e.g., the housing 170 and/or needle hub 270, 370 of FIG. 1A, FIG. 1B, FIG. 2, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, and FIG. 3V herein).

In some embodiments, fewer or more components 550-1, 550-2, 552, 554, 556, 558, 558-1 and/or various configurations of the depicted components 550-1, 550-2, 552, 554, 556, 558, 558-1 may be included in the mixing chamber 550 without deviating from the scope of embodiments described herein. In some embodiments, the components 550-1, 550-2, 552, 554, 556, 558, 558-1 may be similar in configuration and/or functionality to similarly named and/or numbered components as described herein. In some embodiments, the mixing chamber 550 may comprise a portion of a pre-filled dual-chamber medical agent delivery system such as a disposable, single-dose delivery assembly operable to be utilized to execute, conduct, and/or facilitate the method 600 of FIG. 6 herein, and/or portions thereof.

While threads and/or other specific coupling mechanisms between different components are described for purposes of example herein, fewer, more, and/or different types and/or configurations of coupling mechanisms may be utilized without deviating from some embodiments. While different types and/or configurations of coupling mechanisms may be utilized, in some embodiments those specifically described types and/or configurations of coupling mechanisms may provide advantages such as facilitating the execution of the method 600 of FIG. 6 herein, and/or portions thereof. Additionally, while some components that are coupled together are depicted and/or described as being separate and/or distinct components, in some embodiments two or more coupled and/or mated components may be manufactured and/or provided as a single joint and/or integral component, as is or becomes desirable and/or practicable.

III. Pre-Filled Dual-Chamber Medical Agent Delivery Methods

Figure 6:
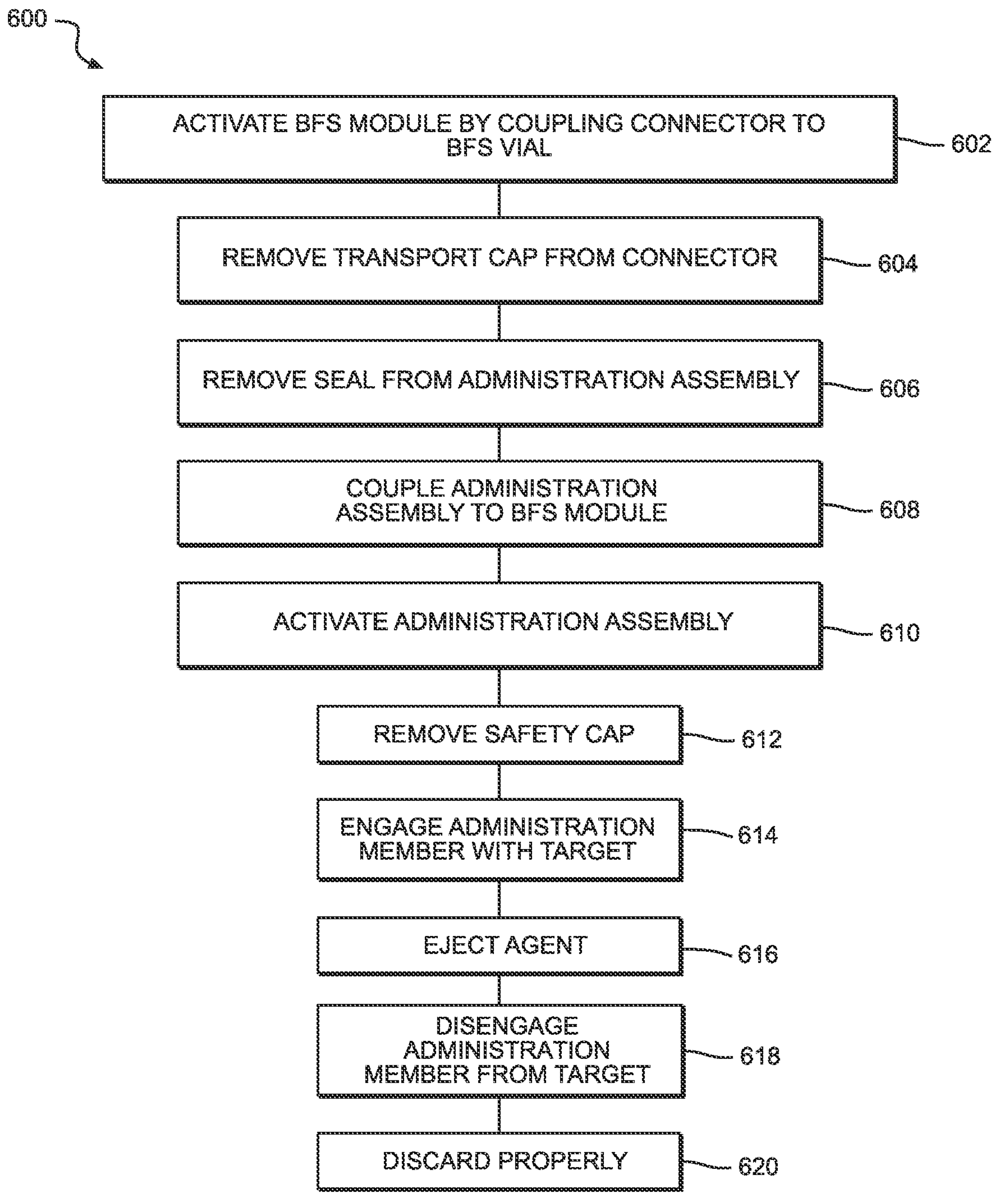
FIG. 6 is a flow diagram of a method according to some embodiments.

Referring now to FIG. 6, a flow diagram of a method 600 according to some embodiments is shown. In some embodiments, the method 600 may be performed and/or implemented by and/or otherwise associated with one or more users such as doctors, nurses, government workers, patients, family members, caregivers, and/or combinations thereof. In some embodiments, the method 600 may be embodied in, facilitated by, and/or otherwise associated with various components and/or systems as described herein. The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure.

In some embodiments, the method 600 may comprise activating and/or defining a BFS module by coupling a connector and a BFS vial, at 602. A BFS (and/or other plastic) bottle, vial, and/or container may, for example, comprise a reservoir and/or volume (e.g., a first chamber) in communication with a neck having a mating feature that snaps into (and/or otherwise selectively couples to) a passage defined by a connector element. According to some embodiments, the BFS vial may be seated in and/or coupled with the connector in a plurality of stages or positions. In at least one stage or position, such as in the case that the BFS vial is fully engaged with the connector, a piercing element of the connector may engage with and pierce (or otherwise rupture or breach) a seal on the neck of the BFS vial. In some embodiments, an axial force exceeding a predefined (e.g., via configuration of the coupling features and/or the piercing element and seal) axial force threshold may be applied to cause the fully engaged state and, accordingly, the piercing of the BFS vial. In some embodiments, piercing of the BFS seal may release and/or expose one or more fluids (e.g., air and/or a liquid agent) stored within the BFS vial to a fluid passage defined by the connector. In some embodiments, an arrow, label, and/or other indication of the activation (e.g., an axial arrow and/or the notation “1” or “Step 1”) action may be provided on the BFS vial and/or the connector.

According to some embodiments, the method 600 may comprise removing a transport cap from the connector, at 604. While a first or proximal end of the connector may be engaged with the BFS vial, for example, a second or distal end thereof may be protected and/or shielded by a seal, cap, and/or cover. In some embodiments, the cover may be disposed to block or seal an outlet port of the connector, such that containments are prevented from entering the connector from the second or distal end (and/or once pierced, and fluid stored within the punctured/opened BFS vial may not escape the second or distal end of the connector). The outlet port may, for example, connect with the fluid passage of the connector, thereby providing fluid communication from the BFS vial to the outlet port. In some embodiments, an arrow, label, and/or other indication of the removal (e.g., an axial arrow and/or the notation “2” or “Step 2”) action may be provided on the transport cap (and/or on the BFS vial and/or the connector).

In some embodiments, the method 600 may comprise removing a seal from an administration assembly, at 606. A mating and/or coupling portion of the administration assembly may be protected by the seal, for example, to prevent contamination of a first or proximal end thereof. According to some embodiments, a second or distal end of the administration assembly may be protected by a removable cap or other seal. In some embodiments, the seal at the first or proximal end of the administration assembly may comprise adhered and/or otherwise affixed foil, paper, wax, and/or any other type of seal that is or becomes known or practicable. In some embodiments, the seal at the first or proximal end of the administration assembly may comprise a tab and/or other removal feature to facilitate removal of the seal by a user. In some embodiments, an arrow, label, and/or other indication of the removal (e.g., an arrow and/or the notation “3” or “Step 3”) action may be provided on the seal (and/or on the administration assembly).

According to some embodiments, the method 600 may comprise coupling the administration assembly to the BFS module, at 608. The exposed second or distal end of the connector may, for example, comprise threads and/or other mating features that correspond to threads and/or mating features disposed on the first or proximate end of the administration assembly. In some embodiments, such as in the case that the administration assembly comprises multiple interconnected components, the connector may be mated and/or coupled with a mixing chamber of the administration assembly. According to some embodiments, the mixing chamber and/or the administration assembly may comprise and/or define an interior volume (e.g., a second chamber) that, other than when covered by the seal, is open at the first or proximal end of the administration assembly. According to some embodiments, the coupling of the administration assembly (and/or the mixing chamber thereof) to the connector may cause the interior volume to become in communication with the outlet port of the connector, thereby placing the first and second chambers in fluid communication with each other. In some embodiments, the mixing chamber (and/or the administration assembly) may house, store, and/or comprise a dry, solid, or gelatinous agent that is disposed within the interior volume thereof. According to some embodiments, the BFS vial (and/or a reservoir thereof) may be squeezed, forcing any liquid in the BFS vial to be ejected through the outlet port of the connector and into the interior volume of the administration assembly (and/or the mixing chamber thereof). In some embodiments, any fluid displaced by the entering liquid agent from the BFS vial may move into the connector and/or the BFS vial. According to some embodiments, the liquid agent from the BFS vial may interact and/or engage with the agent stored in the administration assembly (and/or the mixing chamber thereof), thereby forming and/or defining a combined agent. In the case that the agent stored in the administration assembly (and/or the mixing chamber thereof) comprises a freeze dried or lyophilized agent and the liquid agent from the BFS vial comprises a liquid diluent, for example, the lyophilized agent may be reconstituted by engagement with the liquid diluent. In some embodiments, any two agents (e.g., one from the first chamber and one from the second chamber) may interact due to the coupling of the administration assembly (and/or the mixing chamber thereof) and the BFS module (and/or the connector thereof) and may accordingly define and/or form a combined and/or resultant agent (e.g., a solution, combination, resultant of a chemical reaction, etc.). In some embodiments, an arrow, label, and/or other indication of the coupling (e.g., an arrow and/or the notation "4" or "Step 4") action may be provided on the administration assembly and/or on the BFS module.

In some embodiments, the method 600 may comprise activating the administration assembly (and/or the combined administration assembly and BFS module), at 610. The administration assembly may comprise, for example, an administration member such as a nozzle, spout, dropper, and/or needle that defines an administration channel to provide a flow (or mist, droplet, spray, etc.) of the combined agent to a target such as a patient. According to some embodiments, the administration member (and/or the administration channel thereof) may be separated from the interior volume of the administration assembly (and/or the mixing chamber thereof). The mixing chamber may comprise a seal, plug, and/or blockage at or near a second or distal end of the administration assembly (and/or the mixing chamber thereof), for example, that separates the combined fluid (and/or the individual components thereof) from the administration member until an activation of the administration assembly is effectuated. In some embodiments, the administration assembly may be activated by piercing, breaking, and/or otherwise breaching the seal of the mixing chamber with the administration member. The administration member may, for example, comprise two pointed and/or sharpened ends, one disposed at a distal end of the administration member and one disposed at a proximal end of the administration member, e.g., which itself is oriented adjacent to the seal of the mixing chamber.

According to some embodiments, the administration assembly may comprise separate components that are joined together. The administration assembly may comprise, for example, the mixing chamber and a needle hub that houses the administration member coupled thereto. According to some embodiments, the mixing chamber and the needle hub may be coupled via threads that are at least partially engaged. In some embodiments, a junction at which the threads are at least partially engaged may be sealed with a wrapper and/or other element, such as to prevent premature and/or inadvertent additional engagement of the threads (and/or other coupling features). According to some embodiments, an arrow, label, and/or other indication of the activating (e.g., an arrow and/or the notation "5" or "Step 5") action may be provided on the wrapper at the threaded junction (and/or otherwise on the administration assembly). In some embodiments, the activation may comprise a removal of the wrapper/seal at the threaded junction and a continued threading and/or engagement of the mixing chamber and the needle hub that causes the administration member (and/or a sperate piercing element) to pierce the seal of the mixing chamber. In such a manner, for example, the administration channel may be placed in fluid communication with the mixing chamber and/or interior volume of the administration assembly (and accordingly with the BFS vial as well; in the case that the BFS vial has already been punctured). According to some embodiments, the safety cap may be utilized as a driver to impart rotational force to the needle hub, thereby further engaging any threads engaged between the needle hub and the mixing chamber (and/or otherwise advancing the needle and/or needle hub to pierce the seal of the mixing chamber).

In some embodiments, the method 600 may comprise removing the safety cap, at 612. The safety cap covering the needle (and/or other administration member) may be removed, disengaged, pivoted, rotated, and/or otherwise manipulated to expose the distal or administration end of the administration member, for example. According to some embodiments, an arrow, label, and/or other indication of the removal (e.g., an arrow and/or the notation "6" or "Step 6") action may be provided on the administration assembly and/or on the safety cap (and/or a seal, label, and/or wrapper thereof). In some embodiments, the method 600 may comprise engaging the administration member with a target, at 614. In the case that the administration member comprises a needle, for example, the needle (e.g., the distal and/or engaging end thereof) may be inserted into a target such as a human patient. In the case that the administration member comprises a nozzle or dropper, the administration member may be positioned proximate to the application target (e.g., in a nasal passage, ear, or near any eye). According to some embodiments, the method 600 may comprise ejecting the combined agent, at 616. The BFS vial (and/or a reservoir thereof) may, for example, be squeezed to pressurize the chambers and/or to otherwise force a mixing of the agents (e.g., liquid and dry) and/or an expelling of the combined agent (e.g., a single dose thereof) to the target. In some embodiments, air in a compressible reservoir of the BFS vial may be compressed by a squeezing action (e.g., imparted inward radial force) which forces any liquid agent stored int eh BFS vial to engage with the dry ingredient disposed in the interior volume of the administration assembly. The pressure imparted may force the combined agent (e.g., reconstituted lyophilized agent) through an outlet nozzle of the mixing chamber and into the administration passage, which in turn directs the single dose of the combined agent to the target.

According to some embodiments, the method 600 may comprise disengaging the administration member from the target, at 618. Once the dose of combined agent has been delivered, for example, the administration member may be withdrawn from the target—e.g., uninserted from the target in the case that a needle is employed. In some embodiments, the squeezing and/or ejection pressure or force may be maintained from a predetermined period of time (e.g., five (5) or ten (10) seconds) between engaging and disengaging, to ensure that the single dose is properly and fully dispensed/applied. According to some embodiments, once the administration member is disengaged, any force or pressure may be removed from the BFS vial. In some embodiments, the amounts of fluids (e.g., liquids and/or gases) and dry ingredients may be configured to ensure delivery of a threshold single dose amount of combine agent to the target with the expectation that a designed amount of residual agent (and/or dry ingredient and/or fluids) may remain in the administration assembly and/or the BFS module after application. In other words, some additional agents and/or constituents may be stored in the administration assembly and/or BFS module to account for residuals expected to be retained in the administration assembly and/or BFS module. According to some embodiments, the method 600 may comprise properly discarding the administration assembly and the BFS module (e.g., as a combined single-dose delivery device), at 620. In some embodiments, the safety cap may be reengaged and/or reattached to cover the used needle (or other administration member) tip, e.g., to prevent contamination and/or unintended needle sticks. In some embodiments, the entire system may be discarded into a proper receptacle such as a biohazard and/or sharps disposal unit.

IV. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A pre-filled dual-chamber medical agent delivery system, comprising:

a blow-fill-seal (BFS) bottle defining a radially collapsible fluid chamber having a fluid agent therein, a neck portion, an exterior flange formed on the neck portion, and a BFS seal at an end of the neck portion;

a collar defining a first collar end and a second collar end, the first collar end comprising an interior seat into which the exterior flange is axially mated, the second collar end comprising collar threads, and a penetrating element disposed in an interior collar volume defined by the collar for penetrating the BFS seal of the BFS bottle, the collar further defining an outlet port extending from the second collar end for passage of the fluid agent;

a modular chamber element defining a first chamber end and a second chamber end, the first chamber end comprising first chamber threads operative to be cooperatively mated with the collar threads of the collar, and the modular chamber element defining an interior chamber volume and comprising a chamber seal on an end surface defined at the second chamber end and comprising second chamber threads proximate to the second chamber end;

a needle hub comprising hub threads that are operable to be cooperatively mated with the second chamber threads of the modular chamber element, the needle hub being coupled to a double-ended needle disposed through the needle hub and into the modular chamber element, the needle having a proximal or trailing piercing end and a distal or leading treatment end for application to a patient, the needle defining a needle passage; and a cap covering an administration end of the needle and the cap comprising an interior key that is operable to drive the needle hub to mate the hub threads and the second chamber threads to cause relative movement of the needle from a first transit position to a second activated position;

wherein, in the second activated position, the piercing end of the needle penetrates the chamber seal of the modular chamber element with at least the piercing end of the needle being disposed within the interior chamber volume of the modular chamber element in spaced relation relative to the outlet port of the collar;

wherein compression of the radially collapsible fluid chamber of the BFS bottle causes the fluid agent to be expelled through the outlet port of the collar and collected within the interior chamber volume of the modular chamber element and thereafter through the needle passage of the needle.

2. The pre-filled dual-chamber medical agent delivery system of claim 1, wherein engagement of the cap to drive the mating of the hub threads and the second chamber threads causes the piercing end of the needle to puncture the chamber seal.

3. The pre-filled dual-chamber medical agent delivery system of claim 1, wherein application of an axial force urging the neck portion of the BFS bottle into the interior collar volume causes the penetrating element to pierce the BFS seal.

4. The pre-filled dual-chamber medical agent delivery system of claim 1, further comprising:

a substrate disposed within the interior chamber volume, the substrate comprising an active ingredient;

wherein the fluid agent interacts with the substrate during compression of the radially collapsible fluid chamber of the BFS bottle.

5. The pre-filled dual-chamber medical agent delivery system of claim 4, wherein the active ingredient comprises a lyophilized medical agent deposited on the substrate.

6. The pre-filled dual-chamber medical agent delivery system of claim 4, wherein the BFS bottle contains a first fluid.

7. The pre-filled dual-chamber medical agent delivery system of claim 6, wherein the first fluid comprises air.

8. The pre-filled dual-chamber medical agent delivery system of claim 6, wherein the BFS bottle contains a second fluid.

9. The pre-filled dual-chamber medical agent delivery system of claim 8, wherein the second fluid comprises a diluent.

10. The pre-filled dual-chamber medical agent delivery system of claim 8, wherein an introduction of at least one of the first fluid and the second fluid with the substrate produces a combined agent.

11. The pre-filled dual-chamber medical agent delivery system of claim 1, wherein the BFS bottle further comprises a cylindrical fluid chamber in fluid communication with the collapsible fluid chamber.

12. The pre-filled dual-chamber medical agent delivery system of claim 11, wherein the BFS bottle further comprises a constriction between the cylindrical fluid chamber and the collapsible fluid chamber, wherein the constriction restricts movement of a liquid from the cylindrical fluid chamber to the collapsible fluid chamber.

13. The pre-filled dual-chamber medical agent delivery system of claim 1, wherein the BFS bottle further comprises a side flange extending radially outward on two sides of the BFS bottle.

14. The pre-filled dual-chamber medical agent delivery system of claim 13, wherein the collar further comprises at least one anti-rotation element that engages with at least one of the side flanges of the BFS bottle, limiting rotation of the collar with respect to the BFS bottle.

15. The pre-filled dual-chamber medical agent delivery system of claim 1, wherein the cap is rotatable to cause corresponding movement of the needle hub such that the hub threads and the second chamber threads cooperate to cause movement of the needle from the first transit position to the second activated position.

16. The pre-filled dual-chamber medical agent delivery system of claim 1, including a removable seal mounted to the first chamber end of the modular chamber element to enclose the interior chamber.

17. A pre-filled dual-chamber medical agent delivery system, comprising:

a blow-fill-seal (BFS) bottle defining a radially collapsible fluid chamber having a treatment agent therein, a neck portion, an exterior flange formed on the neck portion, and a BFS seal at an end of the neck portion;

a collar defining a first collar end and a second collar end, the first collar end comprising an interior seat into which the exterior flange is axially mated, the second collar end comprising collar threads, and a penetrating element disposed in an interior collar volume defined by the collar for penetrating the BFS seal of the BFS bottle, the collar further defining an outlet port extending from the second collar end for passage of the treatment agent from the BFS bottle;

a modular chamber element defining a first chamber end and a second chamber end, the first chamber end comprising first chamber threads operative to be cooperatively mated with the collar threads of the collar, and the modular chamber element defining an interior chamber volume for collecting the treatment agent exiting the outlet port of the collar, the modular chamber element comprising a chamber seal on an end surface defined at the second chamber end and comprising second chamber threads proximate to the second chamber end;

a hub comprising hub threads engageable with the second chamber threads of the modular chamber element, the hub including an administration member coupled thereto, the administration member including a proximal or trailing chamber end and a distal or leading administration end for application to a patient; and a cap covering the administration end of the administration member, the cap comprising an interior key configured to engage the hub during rotational movement of the cap to thereby cause corresponding rotational movement of the hub whereby the hub threads of the hub threadably engage the second chamber threads of the modular chamber element to move the hub and the administration member from a first transit position to a second activated position, wherein, in the second activated position, the chamber end of the administration member penetrates the chamber seal of the modular chamber element;

wherein the chamber end of the administration member is disposed within the interior chamber volume of the modular chamber in spaced relation relative to the outlet port of the collar when in the second activated position of the hub and the administration member to access the treatment agent collected in the interior chamber volume of the modular chamber element.

18. The pre-filled dual-chamber medical agent delivery system of claim 17, wherein application of an axial force urging the neck portion of the BFS bottle into the interior collar volume causes the penetrating element to penetrate the BFS seal.

19. The pre-filled dual-chamber medical agent delivery system of claim 17, further comprising:

a substrate disposed within the interior chamber volume, the substrate comprising an active ingredient;

wherein the treatment agent interacts with the substrate during compression of the radially collapsible fluid chamber of the BFS bottle.

20. The pre-filled dual-chamber medical agent delivery system of claim 17, wherein the treatment agent comprises a first fluid and a second fluid, the second fluid different from the first fluid.

* * * * *